United States Patent
Breipohl et al.

(10) Patent No.: US 6,316,595 B1
(45) Date of Patent: Nov. 13, 2001

(54) PNA SYNTHESIS USING A BASE-LABILE AMINO PROTECTING GROUP

(75) Inventors: Gerhard Breipohl, Frankfurt; Eugen Uhlmann, Glashütten; Jochen Knolle, Kriftel, all of (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/495,457

(22) Filed: Feb. 1, 2000

Related U.S. Application Data

(62) Division of application No. 08/967,197, filed on Oct. 29, 1997, now Pat. No. 6,121,418, which is a continuation of application No. 08/402,844, filed on Mar. 13, 1995, now abandoned.

(30) Foreign Application Priority Data

Mar. 14, 1994 (DE) ................................. 44 08 533

(51) Int. Cl.$^7$ ....................................... C07K 1/00
(52) U.S. Cl. ................... 530/333; 562/553; 562/561; 530/338; 536/18.7; 544/264
(58) Field of Search .................. 530/333, 338; 562/553, 561; 536/18.7; 544/264

(56) References Cited

U.S. PATENT DOCUMENTS

| | | | |
|---|---|---|---|
| 5,527,675 | 6/1996 | Coull | 435/6 |
| 5,539,082 | 7/1996 | Nielsen | 530/300 |
| 5,539,083 | 7/1996 | Cook | 530/333 |

FOREIGN PATENT DOCUMENTS

| | | |
|---|---|---|
| 0 187 130 | 9/1986 | (EP) . |
| 0 264 802 | 4/1988 | (EP) . |
| 0 287 822 | 10/1988 | (EP) . |
| 0 322 348 | 6/1989 | (EP) . |
| 0 460 446 | 12/1991 | (EP) . |
| 93307455.1 | 9/1993 | (GB) . |
| WO 92/20702 | 11/1992 | (WO) . |
| WO 93/12129 | 6/1993 | (WO) . |

OTHER PUBLICATIONS

Thomson, Tetrahedron 51: 6179 (1995).
Gross, The Peptides, vol. 3, pp. 21–24, 84–88, 223–229 (1981).
W.S. Saari et al., "Cyclization–Activated Prodrugs. Basic Esters of 5–Bromo–2'deoxyuridine," Journal of Medicinal Chemistry, vol. 33, No. 9, pp. 2590–2595 (1990).
E.P. Heimer et al., "Synthesis of Analogs and Oligomers of N–(2–amino–ethyl) Glycine and Their Gastrointestinal Absorption in the Rat," vol. 23, pp. 203–211 (1984).
Chris Meier et al., "Peptide Nucleic Acids (PNAs)—Unusual Properties of Nonionic Oligonucleotide Analogues," Angewandte Chemie, vol. 31, No. 8, pp. 1008–1010 (Aug. 1992).
Michael Egholm et al., "Peptide Nucleic Acids (PNA) Oligonucleotide Analogues with an Achiral Peptide Backbone," Journal of the American Chemical Society, vol. 114, No. 5, pp. 1895–1897, (Feb. 1992).
Kim Dueholm et al., "Synthesis of Peptide Nucleic Acid Monomers Containing the Four Natural Nucleobases: Thymine, Cytosine, Adenine, and Guanine and Their Oligomerization," vol. 59, No. 19, pp. 5767–5773 (Sep. 1994).
Hanvey, Science 258, 1481 (1992).
Barany, Int. J. Pept. Prot. Res. 30, 705 (1987).
Nielsen Science 254, 1497 (1991).
Egholm et al., "Recognition of Guanine and Adenine in DNA by Cystosine and Thymine Containing Peptide Nucleic Acids (PNA)", J. Am. Chem. Soc., 114, pp. 9677–8678 (1992).
König et al., "Recent Experiences in Peptide Synthesis", Proceedings of the Akabori Conference Grainau–Eibsee/Bavaria, Jun. 12–13, pp. 32–35 (1995).
Ramage et al., "A Base Labile Protecting Group for Peptide Synthesis: 2, 2–Bis(4'–nitrophenyl)ethan–1–oxycarbonyl Urethanes", Tetrahedron, vol. 47, pp. 8001–8024 (1991).
Acedo et al., "N–2(2,4–Dinitrophenyl)ethyloxycarbonyl–1–Amino Acids, New Labile Protected Derivatives Suitable for Solid–Phase Peptide Synthesis", Tetrahedron, vol. 33, pp. 4989–4992 (1992).
Bycroft et al., "A Novel Lysine–Protecting Procedure for Continuous Flow Solid Phase Synthesis of Branched Peptides", J. Chem. Soc., Chem. Commun., pp. 778–779 (1993).
Merrifield, "Solid Phase Peptide Synthesis. I. The Synthesis of a Tetrapeptide", J. Am. Chem. Soc., 85, pp. 2149–2154 (1963).
Jung et al., "Methoden der Multiplen Peptidsynthese und ihre Anwedungen" Agnew. Chem., 104, pp. 375–391 (1992).
Barlos et al., "Darstellung neuer säureempfindlicher Harze vom sek.–Alkohol–Typ und ihre Anwendung zur Synthese von Peptiden", Liebigs Ann. Chem., pp. 951–955 (1989).
Rink, "Solid–Phase Synthesis of Protected Peptide Fragments Using a Trialkoxy–Diphenyl–Methylester Resin", Tetrahedron Letters, vol. 28, pp. 3787–3790 (1987).
Breipohl et al., "Solid Phase Synthesis of Peptide Aminoalkylamides Development and Application of New Linking Agents", Tetrahedron Letters, vol. 28, pp. 5647–5650 (1987).

(List continued on next page.)

Primary Examiner—Christopher S. F. Low
Assistant Examiner—David Lukton
(74) Attorney, Agent, or Firm—Finnegan, Henderson, Farabow, Garrett and Dunner, L.L.P.

(57) ABSTRACT

The invention provides compounds and processes for synthesis of peptide nucleic acids (PNA). The compounds include temporary amino protecting groups that are base-labile, and protection groups for the exocyclic amino function of the nucleotide base that is compatible with the base-labile amino protecting group. Cleavage of an oligomer comprising these compounds from a solid support can be achieved using weak or medium strength acids.

33 Claims, No Drawings

OTHER PUBLICATIONS

Breipohl et al., "Synthesis and Application of Acid Labile Anchor Groups for the Synthesis of Peptide Amides by Fmoc–Solid–Phase Peptide Synthesis", Int. J. Peptide Protein Res., 34, pp. 262–267 (1989).

Stüber et al., "Synthesis of Peptide Amides by Fmoc–Solid–Phase Peptide Synthesis and Avid Labile Anchor Groups", Int. J. Peptide Protein Res., 34, pp. 215–221 (1989).

Barany et al., "Solid–Phase Peptide Synthesis: A Silver Anniversary Report", Int. J. Peptide Protein Res., 30, pp. 705–739, (1987).

Fields et al., "Solid Phase Peptide Synthesis Utilizing 9–Fluorenylmethoxycarbonyl Amino Acids", Int. J. Peptide Protein Res., 35, pp. 161–214, (1990).

Castro et al., "Reactifs De Couplage Peptidique IV", Tetrahedron Letters, 14, pp. 1219–1222, (1975).

Coste et al., "PyBOP®: A New Peptide Coupling Reagent Devoid of Toxic By–Product", Tetrahedron Letters, vol. 31, 2, pp. 205–208 (1990).

Coste et al., "BROP: A New Reagent for Coupling N–Methylated Amino Acids", Tetrahedron Letters, vol. 31, 5, pp. 669–672, (1990).

Coste et al., "Oxybenzotriazole Free Peptide Coupling Reagents for N–methylated Amino Acids", Tetrahedron Letters, vol. 32, 17, pp. 1967–1970 (1991).

Dourtoglou et al., "O–Benzotriazolyl–N,N,N', N'–tetramethyluronium Hexafluorophosphate as Coupling Reagent for the Synthesis of Peptides of Biological Interest", Communications, pp. 572–574, (1984).

Knorr et al., "New Coupling Reagents in Peptide Chemistry", Tetrahedron Letters, pp. 1927–1930, (1989).

Carpino, "1–Hydroxy–7–Azabenzotriazole. An Efficient Peptide Coupling Additive", J. Am. Chem. Soc., 115, pp. 4397–4398, (1993).

Ehrlich et al., "Synthesis of Cyclic Peptides Via Efficient New Coupling Reagents", Tetrahedron Letters, vol. 34, 30, pp. 4781–4784, (1993).

Akaji et al., "Anchoring of Fmoc Amino Acid to 4–Alkoxybenzyl Alcohol Resin Using a New Esterification Reagent", Tetrahedron Letters, vol. 33, 22, pp. 3177–3180, (1992).

Blankemeyer–Menge et al., "An Efficient Method for Anchoring Fmoc–Amino Acids to Hydroxyl–Functionalised Solid Supports", Tetrahedron Letters, vol. 21, 12, pp. 1701–1704, (1990).

Kirstgen et al., "Use of Esters of 2,5–Diphenyl–2, 3–dihydro–3–oxo–4–hydroxythiophene Dioxide in Solid Phase Peptide Synthesis. A New Procedure for Attachment of the First Amino Acid", J. Chem. Soc., Chem. Commun., pp. 1870–1871, (1987).

Hudson et al., "Methodological Implications of Simultaneous Solid–Phase Peptide Synthesis: A Comparison of Active Esters", Peptide Research, vol. 3, 1, pp. 51–55, (1990).

König et al., "Eine Neue Methode Zur Synthese von Peptiden: Aktivierung der Carboxylgruppe Mit Dicyclohexycarbodiimid unter Zusatz von 1–Hydroxy–benzotriazolen", Chem. Ber., 103, pp. 788–798, (1970).

König et al., "Eine Neue Methode Zur Synthese von Peptiden: Aktivierung der Carboxylgruppe Mit Dicyclohexycarboniimid und 3–Hydroxy–4–oxo–3, 4–4–dihydro–1.2.3–benzotriazin", Chem. Ber., 103, pp. 2034–2040, (1970).

JCBN "Nomenclature and Symbolism for Amino Acids and Peptides", Eur. J. Biochem., 138, pp. 9–37, (1984).

Curran, Tetrahedron Letters 35, 5409–5412, 1994.*

* cited by examiner

PNA SYNTHESIS USING A BASE-LABILE AMINO PROTECTING GROUP

This is a division of application Ser. No. 08/967,197, filed Oct. 29, 1997 now U.S. Pat. No. 6,121,418, which is a continuation of application Ser. No. 08/402,844, filed Mar. 13, 1995, now abandoned, all of which are incorporated herein by reference.

Peptide nucleic acids (PNA) are compounds which are analogs of DNA in which the deoxyribose phosphate skeleton has been replaced by a peptide oligomer. The syntheses which have thus far been described in the literature (Michael Egholm, Peter E. Nielsen, Ole Buchardt and Rolf H. Berg, J. Am. Chem. Soc. 1992, 114, 9677–9678; Ole Buchardt, Michael Egholm, Peter E. Nielsen and Rolf E. Berg, WO 92/20702) use the acid-labile tert-butyloxycarbonyl (Boc) protecting group, which is eliminated with medium-strength acids such as, for example, trifluoroacetic acid, for temporarily protecting the amino group of the monomer. Solid phase synthesis of oligomers then follows tho customary peptide synthesis method as described, for example, by Merrifield (B. Merrifield, J. Am. Chem. Soc., 1963, 85, 2149). A strong acid, usually liquid hydrogen fluoride, is used in this case to cleave the PNA oligomer from the solid support. As a consequence, these reaction conditions, in particular the repeated treatment with trifluoroacetic acid, do not permit a reaction in open reaction vessels, as is the case, for example, when multiple peptide synthesizers are employed (review: G. Jung and A. Beck-Sickinger, Angew. Chem. 104 (1992) 375–391).

The object of the invention is to develop a synthesis process which uses a base-labile, temporary amino protecting group for constructing the PNA oligomers and which permits cleavage of the oligomer from the solid support using weak or medium-strength acids.

The subsequent invention describes a process for preparing PNA oligomers of the formula I

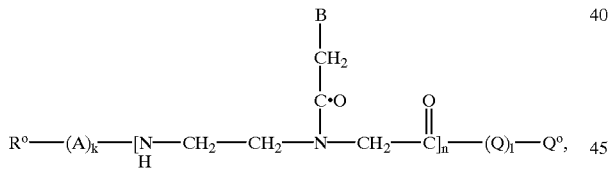

(I)

in which
R⁰ is hydrogen, $C_1$–$C_{18}$-alkanoyl, $C_1$–$C_{18}$-alkoxycarbonyl, $C_3$–$C_8$-cycloalkanoyl, $C_7$–$C_{15}$-aroyl, $C_3$–$C_{13}$-heteroaroyl, or a group which favors intracellular uptake of the oligomer or interacts with the target nucleic acid drawing hybridazation;
A is an amino acid residue, preferably from the group glycine, leucine, histidine, phenylalanine, cysteine, lysine, arginine, aspartic acid, glutamic acid, proline, tetrahydroquinoline-3-carboxylic acid, octahydroindole-2-carboxylic acid and N-(2-aminoethyl)glycine;
k is an integer from 0 to 20, preferably from 0 to 10;
Q is an amino acid residue, preferably from the group glycine, leucine, histidine, phenylalanine, cysteine, lysine, arginine, aspartic acid, glutamic acid, proline, tetrahydroquinoline-3-carboxylic acid, octahydroindole-2-carboxylic acid and N-(2-aminoethyl)glycine;
l is an integer from 0 to 20, preferably from 0 to 10;
B is a nucleotide base which is customary in nucleotide chemistry, for example natural nucleotide bases such as adenine, cytosine, guanine, thymine and uracil, or unnatural nucleotide bases such as purine, 2,6-diaminopurine, 7-deazaadenine, 7-deazaguanine, $N^4,N^4$-ethanocytosine, $N^6,N^6$-ethano-2,6-diaminopurine, 5-methylcytosine, 5-($C_3$–$C_6$)-alkynyluracil, 5-($C_3$–$C_6$)-alkynylcytosine, 5-fluorouracil or pseudoisocytosine, 2-hydroxy-5-methyl-4-triazolopyrimidine, or their prodrug forms;
Q⁰ is hydroxyl, NH₂ or NHR″, with R″=$C_1$–$C_{18}$-alkyl, $C_2$–$C_{18}$-aminoalkyl or $C_2$–$C_{18}$-hydroxyalkyl; and
n is an integer of 1–50, preferably 4–35,
wherein either amino acids (Q') are first coupled, using a method which is customary for solid phase synthesis, to a polymeric support of the formula II

which is provided with an anchor group L which contains the radical Q⁰ in a latent manner, to result in, as an intermediate, a compound of the formula III

in which L is defined as above, Q' is an amino acid Q which is, where appropriate, protected in its side chain, and l is an integer from 0 to 20, and
a) a compound of the formula IV

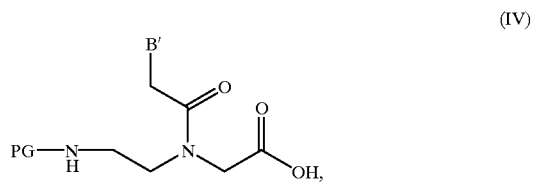

in which
PG is a base-labile amino protecting group, and
B' is a nucleotide base which is protected on the exocyclic amino function, is then coupled onto the compound of the formula III, or a compound of the formula IV is coupled directly to the polymeric support of the formula II, using the coupling reagents which are customary in peptide chemistry,
b) the temporary, base-labile protecting group PG is eliminated using a suitable reagent,
c) steps a and b are repeated n−1 times,
d) further amino acids A', which are defined as A but are, where appropriate, protected in their side chains, are coupled on using a method which is customary for solid phase synthesis and then, if R⁰ is not hydrogen, the radical R⁰ is introduced using a customary method,
e) the compound of the formula I is cleaved, out of the compound of the formula Ia

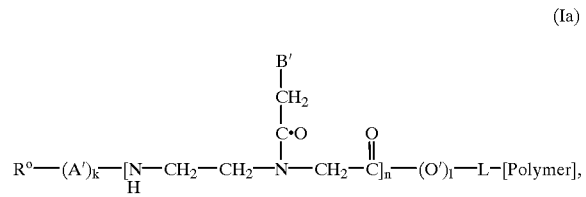

which is obtained as intermediate compound and in which $R^0$, A', k, B', n, Q' and l are defined as above and L is an anchor group, from the polymeric support using a cleaving reagent, with the protecting groups which are, where appropriate, present on the exocyclic amino function of the nucleotide bases and on the side chains of the amino acids being eliminated simultaneously or else subsequently.

Examples of groups which favor the intracellular uptake of the oligomer are alkanoyl and alkoxycarbonyl compounds having various lipophilic radicals such as —$(CH_2)_x$—$CH_3$, in which x is an integer of 6–18, —$(CH_2)_n$—CH=CH—$(CH_2)_m$—$CH_3$, in which n and m, independently of each other, are an integer from 6 to 12, —$(CH_2CH_2O)_4$—$(CH_2)_9$—$CH_3$, —$(CH_2CH_2O)_8$—$(CH_2)_{13}$—$CH_3$ and —$(CH_2CH_2O)_7$—$(CH_2)_{15}$—$CH_3$, and also steroid residues, such as cholesteryl, or vitamin residues, such as vitamin E, vitamin A or vitamin D, and other conjugates which make use of natural carrier systems, such as bile acid, folic acid, 2-(N-alkyl, N-alkoxy)-amino-anthraquinone, and conjugates of mannose and peptides of the corresponding receptors which lead to receptor-mediated endocytosis of the oligomers, such as EGF (epidermal growth factor), bradykinin and PDGF (platelet derived growth factor). Labeling groups are understood to mean fluorescent groups, for example of dansyl-(N-dimethyl-1-aminonaphthyl-5-sulfonyl-)derivatives, fluorescein derivatives or coumarin derivatives, or chemiluminescent groups, for example of acridine derivatives, as well as the digoxygenin system, which can be detected using ELISA, the biotin group, which can be detected using the biotin/avidin system, or else linker arms having functional groups which allow subsequent derivatization with detectable reporter groups, for example an aminoalkyl linker which is reacted with an active acridinium easter to form a chemiluminescent probe. Typical labeling groups are:

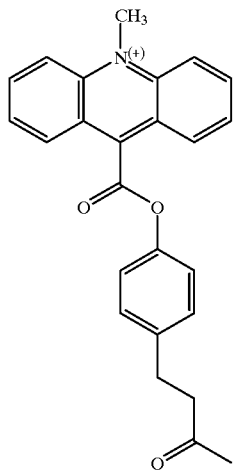

Acridinium ester

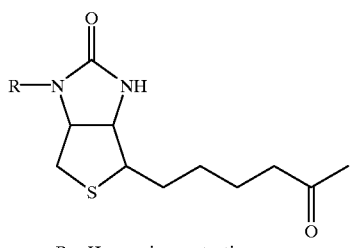

R = H or amino protecting group
Biotin conjugate (= "biotin" for R = Boc

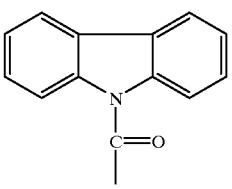

Carbazole derivative

Groups which upon hybridization of the oligomer with the target nucleic acid attack the latter by binding, cross-linking or clearing are for example conjugates of acridine, psoralene, phenanthridine, naphthoquinone, daunomycin or chloroethylaminoaryl. Typical intercalating and crosslinking residues are:

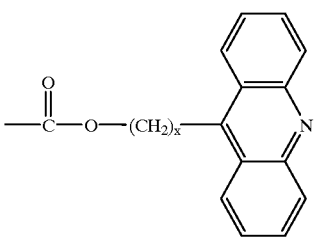

acridine derivative x = 2 – 12, preferably 4

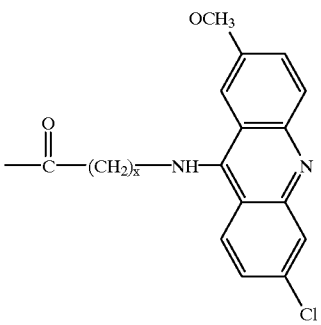

x = 2 – 12, preferably 4

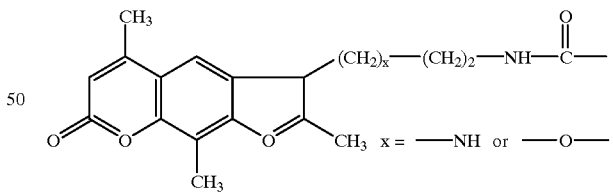

Trimethylpsorolene conjugate (= "psorolene" for x = 0)

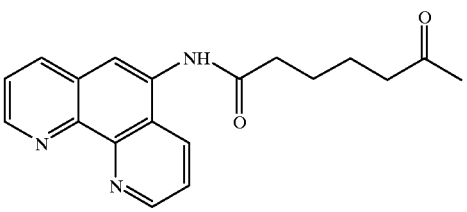

Phenonthroline conjugate

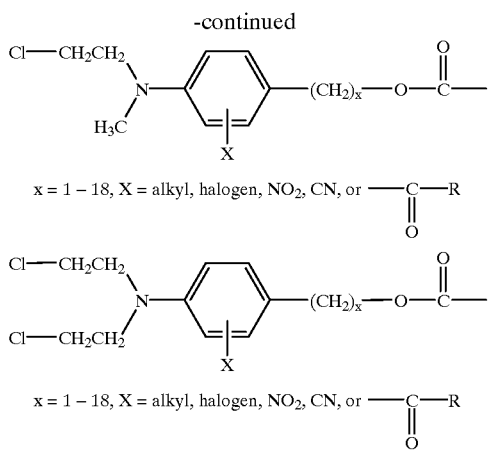

x = 1 – 18, X = alkyl, halogen, NO$_2$, CN, or —C(=O)—R x = 1 – 18, X = alkyl, halogen, NO$_2$, CN, or —C(=O)—R Anchor groups L, which contain the function $Q^0$ in a latent manner, are described, for example, in George Barany, Nancy Kneib-Cordonier and Daniel G. Mullen, Int. J. Peptide Protein Res., 1987, 30, 705–739; Gregg B. Fields and Richard L. Noble, Int. J. Peptide Protein Res. 35, 1990, 161–214; K. Barlos, D. Gatos, J. Hondrelis, J. Matsoukas, G. J. Moore, W. Schafer and P. Botiriou, Liebigs Ann. Chem. 1989, 951–955; H. Rink, Tetrahedron Lett. 1987, 3787–3790; G. Breipohl, J. Knoll. and R. Geiger, Tetrahedron Lett. 1987, 5647–5650; G. Breipohl, J. Knolle and W. Stüber, Int. J. Peptide Protein Res., 1989, 34, 262–267; W. Stüber, J. Knolle and G. Breipohl, Int. J. Peptide Protein Res., 1989, 34, 215–220 or in EP-A-0 264 802 (HOE 86/F259), EP-A-0 287 882 (HOE 86/F101) and EP-A-0 322 348 (HOE 87/F386K).

Examples of polymeric supports which are provided with an anchor group, which contains the group $Q^0$ in a latent manner, are 4-alkoxybenzyl alcohol resin, 2-methoxy-4-alkoxybenzyl alcohol resin, 2-chlorotriphonylmethyl resin, 2,4-dimethoxybenzhydrylamine resin or 4-(2',4'-dimethoxyphenylaminomethyl)phenoxymethyl resin, or the polymeric supports which are functionalized with a primary amino group, such as, for example, ®polyHIPE, ®Tentagel, ®Controlled Pore Glass or polystyrene, onto which one of the anchor groups which contain the group $Q^0$ in a latent manner, such as, for example, 4-(4'-methoxybenzhydryl)phenoxyacetic acid, 4-(4'-methoxybenzhydryl)phenoxybutyric acid, 4-hydroxymethylphenoxyacetic acid, 2-methoxy-4-hydroxymethylphenoxyacetic acid, 5-(4-aminomethyl-3,5-dimethoxyphenoxy)valeric acid, 3-(amino-4-methoxybenzyl)-4-methoxyphenylpropionic acid, 5-(amino-4-methoxybenzyl)-2,4-dimethoxyphonylpropionic acid, 4-(amino-($C_2$–$C_8$)alkylaminocarbonyloxymethyl)phenoxyacetic acid, mono(amino-$C_2$–$C_{16}$-alkyl)oxalate or mono(amino-$C_2$–$C_{16}$-alkyl)succinate is coupled.

The following anchor groups, or anchor groups which are already bonded to the polymeric support, are preferably used: 4-alkoxybenzyl alcohol resin, methoxy-4-alkoxybenzyl alcohol resin or 2-chlorotriphenylmethyl resin, or the anchor groups 4-(4'-methoxybenzhydryl)phenoxybutyric acid, 4-hydroxymethylphenoxyacetic acid, 2-methoxy-4-hydroxymethylphenoxyacetic acid, 5-(amino-4-methoxybenzyl)-2,4-dimethoxyphenylpropionic acid, 4-(amino-($C_2$–$C_8$)-alkylaminocarbonyloxymethyl)phenoxyacetic acid, mono(amino-$C_2$–$C_{16}$-alkyl)oxalate or mono(amino-$C_2$–$C_{16}$-alkyl)succinate, which contain the group $Q^0$ in a latent manner and which are coupled onto a support of the ®Tentagel, ®Controlled Pore Glass or polystyrene type which is functionalized with a primary amino group.

Examples of base-labile amino protective groups PG are 9-fluorenylmethoxycarbonyl (Pmoc) and 2,2-[bis(4-nitrophenyl)]ethoxycarbonyl (Bnpeoc) (W. König, D. B ücher, R. Knüttel, K. Lindner and A. Volk, Proceedings of the Akabori Conference, Grainau-Eibsee/Bavaria, Jun. 12–13, 1985, p. 32 and R. Ramage, A. J. Blake, M. R. Florence, Th. Gray, G. Raphy and P. L. Roach, Tetrahedron 1991, 37, 8001–8024), 2-(2,4-dinitrophonyl)ethoxycarbonyl (Dnpeoc) (M. Acedo, F. Albericio, R. Eritja, Tetrahedron Lett. 1992, 4989–4992), 2-methylsulfonylethyloxycarbonyl (Msc) and 1-(4,4-dimethyl-2,6-dioxocyclohexylidene)ethyl (Dde) (B. W. Bycroft, W. C. Chan, S. R. Chabra and N. D. Home, J. Chem. Soc., Chem. Commun. 1993, 778–779); the use of Fmoc, Bnpeoc and Dnpooc is preferred, with the Fmoc protecting group being very particularly preferably used.

The activation methods which were used in step a of the above synthesis process, and which are customary in peptide synthesis, are described, for example, in Houben-Weyl, Methoden der organischen Chemie [Methods of organic chemistry], volume 15/2, Georg Thieme Verlag Stuttgart 1974. Further reagents, such as, for example, BOP (B. Castro, J. R. Dormoy, G. Evin and C. Selve, Tetrahedron Lett. 1975, 1219–1222), PyBOP (J. Coste, D. Le-Nguyen and B. Castro, Tetrahedron Lett. 1990, 205–208), BroP (J. Coste, M.-N. Dufour, A. Pantaloni and B. Castro,, Tetrahedron Lett. 1990, 669–672) ar PyBroP (J. Coste, E. Frerot, P. Jouin and B. Castro, Tetrahedron Lett. 1991, 1967–1970) and uronium reagents, such as, for example, HBTU (V. Dourtoglou, B. Gross, V. Lambropoulou, C. Zioudrou, Synthesis 1984, 572–574), TBTU, TPTU, TSTU, TNTU (R. Knorr, A. Trzeciak, W. Bannwarth and D. Gillessen, Tetrahedron Letters 1989, 1927–1930), TOTU (EP-A-0 460 446), HATU (L. A. Carpino, J. Am. Chem. Soc. 1993, 115, 4397–4398), HAPyU, TAPipU (A. Ehrlich, S. Rothemund, M. Brudel, M. Beyermann, L. A. Carpino and M. Bienert, Tetrahadran Lott. 1993, 4781–4784) or BOI (K. Akaji, N. Kuriyama, T. Kimura, Y. Fujiwara and Y. Kiso, Tetrahedron Lett. 1992, 3177–3180) or acid chlorides or acid fluorides (L. A. Carpino, H. G. Chao, M. Beyermann and M. Bienert, J. Org. Chem., 56 (1991), 2635; J.-N. Bertho, A. Loffet, C. Pinel, P. Reuther and G. Sennyey in E. Giralt and D. Andreu (Eds.) Peptides 1990, Escom Science Publishers B. V. 1991, pp. 53–54; J. Green and K. Bradley, Tetrahedron 1993, 4141–4146), 2,4,6-mesitylenesulfonyl-3-nitro-1,2,4-triazolide (MSNT) (B. Blankemeyer-Menge, M. Nimitz and R. Frank, Tetrahedron Lett. 1990, 1701–1704), 2,5-diphenyl-2,3-dihydro-3-oxo-4-hydroxythiophene dioxide (TDO) (R. Kirstgen, R. C. Sheppard, W. Steglich, J. Chem. Soc. Chem. Commun. 1987, 1870–1871), or activated esters (D. Hudson Peptide Res. 1990, 51–55) are described in the relevant literature references. The use of carbodiimides, for example dicyclohexylcarbodiimide or diisopropylcarbodiimide, is preferred. Phosphonium reagents, such as, for example, PyBOP or PyBroP, uronium reagents, such as, for example, HBTU, TBTU, TPTU, TSTU, TNTU, TOTU or HATU, BOI or acid chlorides or acid fluorides are likewise preferably used.

In this context, the coupling can be carried out directly by adding an amino acid derivative or a PNA monomer of the formula IV, together with the activating reagent and, where appropriate, with the addition of additives such as, for example, 1-hydroxybenzotriazole (HOBt) (W. König, R. Geiger, Chem. Ber. 103, 788 (1970)) or 3-hydroxy-4-oxo-3,4-dihydrobenzotriazine (HOOBt) (W. König, R. Geiger, Chem. Ber. 103, 2034 (1970)), to the resin, or else the structural component can be separately preactivated to form the activated ester, and the solution of the activated species can be added, in a suitable solvent, to the polymer which is capable of coupling.

Protecting groups which are compatible with the base-labile amino protecting group PG, such as, for example, protecting groups, which are labile to weak or medium strength acids, of the urethane type, such as tert-butyloxycarbonyl (Boc), 4-methoxybenzyloxycarbonyl (Moz) or 3,5-dimethoxyphenyl-2-propyl-2-oxycarbonyl (Ddz), or of the trityl type, such as triphenylmethyl (Trt), (4-methoxyphenyl)diphenylmethyl (Mmt), (4-methylphenyl)-diphenylmethyl (Mtt), di-(4-methoxyphenyl)phenylmethyl (Dmt) or 9-(9-phenyl) xanthenyl (pixyl) are used for protecting the exocyclic amino function in the nucleotide bases B' which are protected in their exocyclic amino function. The use of butyloxycarbonyl (Boc), triphenylmethyl (Trt), (4-methoxyphenyl)diphenylmethyl (Mmt), (4-methylphenyl)diphenylmethyl (Mtt) or di-(4-methoxyphenyl)phenylmethyl (Dmt) is particularly preferred, with Trt, Mtt, Mmt and Dmt surprisingly effecting a marked improvement in the solubility of the monomers. The use of (4-methoxyphenyl)diphenylmethyl (Mmt) is very particularly preferred.

Examples of reagents for eliminating the base-labile amino protecting group PG are a solution of piperidine, morpholine, hydrazine or 1,8-diazabicyclo[5.4.0]undec-7-ene (DBU) in dimethylformamide, N-methylpyrrolidinone (NMP), acetonitrile (ACN) or dichloromethane (DCM); the use of 20% piperidine in DMP or N-methylpyrrolidinone and also of a mixture of 2% DBU and 2% piperidine in DMP or 0.1M DBU in DMF or 0.1M DBU in dichloromethane is particularly preferred for the Fmoc, Dnpeoc and Bnpeoc protecting groups.

The coupling-on of the amino acid residues Q' and A' of the formula Ia is effected using amino acid derivatives which preferably carry the same amino protecting group PG which is also used for the compounds of the formula IV. Any side chain functions of the amino acids which are present are provided with a protecting group, such as, for example, Boc, Moz, OtBu, tBu, Trt, Mtr or Pmc which is labile to weak to medium-strength acids. In this context, amino acid derivatives such as PG-Gly-OH, PG-Lys(Boc)-OH, PG-Arg(Mtr)-OH, PG-Arg(Pmc)-OH, PG-Arg(Trt)-OH, PG-Cys(Trt)-OH, PG-Asp(OtBu)-OH, PG-Glu(OtBu)-OH or PG-Aeg(Boc)-OH, PG-His(Trt)-OH, in which PG has the above meaning, are preferred. The following amino acid derivatives Fmoc-Gly-OH, Fmoc-Lys(Boc)-OH, Fmoc-Arg(Mtr)-OH, Fmoc-Arg(Pmc)-OH, Fmoc-Arg(Trt)-OH, Fmoc-Cys(Trt)-OH, Fmoc-Asp(OtBu)-OH, Fmoc-Glu(OtBu)-OH and Fmoc-Aeg(Boc)-OH, Fmoc-His(Trt)-OH are very particularly preferred in this present case.

The compounds of the formula IV

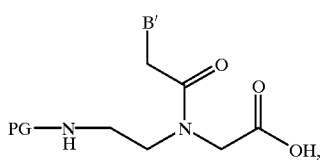

(IV)

which are employed in the above described synthesis process and in which
PG is a base-labile amino protecting group, and
B' is a nucleotide bass which is protected on the exocyclic amino function, are novel.

The compounds of the formula IV

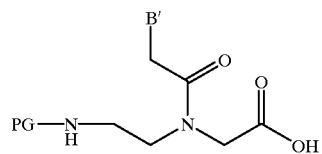

(IV)

are obtained by reacting a compound of the formula V

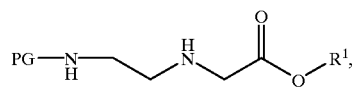

(V)

in which
PG is a base-labile amino protecting group, and
$R^1$ is an ester protecting group, such as, for example, methyl, ethyl, butyl, 2-(methoxyethoxy)ethyl, benzyl, preferably methyl or 2- (methylethoxy)ethyl, particularly preferably methyl,
with a compound of the formula VI

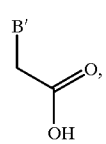

(VI)

in which
B' is a nucleotide base, with the exocyclic amino function of the nucleotide base being protected by a protecting group which is compatible with the base-labile amino protecting group, such as, for example, protecting groups, which are labile to weak acids, of the urethane type, such as Boc or Moz, or of the Trityl type, such as Trt, Mmt, Dmt or pixyl,
at 0–45° C., preferably at room temperature, in a suitable solvent such as, for example, DMF, acetonitrile, dichloromethane or mixtures of these solvents, using one of the coupling reagents which is customary in peptide chemistry, such as, for example, carbodiimides, phosphonium reagents, uronium reagents, acid halides or activated esters, to yield a compound of the formula VII

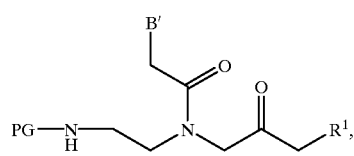

(VII)

in which
PG, B' and R' are defined as above, and, subsequently, eliminating the ester protecting group $R^1$ using alkali metal hydroxide solution, or else enzymatically using esterases or lipases at 8–50° C. in a suitable solvent such as, for example, dioxane, water, tetrahydrofuran, methanol, water or mixtures of these solvents.

A further option for synthesizing the compound of the formula IV comprises reacting a compound of the formula V

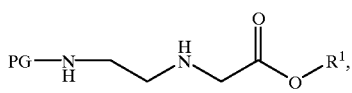 (V)

in which

PG is a base-labile amino protecting group with the above meaning, and

R¹ is hydrogen or a temporary silyl protecting group, such as, for example, trimethylsilyl, with a compound of the formula VIII

 (VIII), in which

B' is defined as in formula VI, and

R² is halogen, such as, for example, fluorine, chlorine or bromine, or the radical of an active ester, such as, for example, OBt, OObt, OPfp or ONSu, at 0–40° C., preferably 20–30° C., in a suitable solvent such as, for example, DMF, NMP, acetonitrile, dichloromethane or mixtures of these solvents. In this context, the temporary protection of the acid function in compounds of the formula V can be effected by reaction with customary silylating reagents, such as, for example, bis(trimethylsilyl)acetamide. This temporary protecting group is eliminated after the compounds of the formula VIII have reacted by adding water or alcohols to the reaction mixture.

For synthesis of the compounds of the formula V, aminoethylglycine or the corresponding aminoethylglycine ester is provided with the appropriate base-labile protecting group. In this context, the base-labile protecting group is introduced using a partial modification of a method known from the literature. Examples of suitable reagents are Fmoc-Cl, Fmoc-ONSu, Bnpeoc-ONSu, Dnpeoc-ONSu, Msc-Cl and 2-acetyldimedone (Dde). In this reaction, the solubility of the aminoethylglycine can be improved, while at the same time protecting the acid function, by reacting with customary silylation reagents such as, for example, bis(trimethylsilyl)acetamide. This temporary protecting group is eliminated, after reacting with the protecting group reagents, by adding water or alcohols to the reaction mixture. The aminoethylglycine used as starting material, or the corresponding aminoethylglycine ester, are prepared by a method known from the literature (E. P. Heimer, H. E. Gallo-Torres, A. M. Felix, M. Ahmad, T. J. Lambros, F. Scheidl and J. Meienhofer Int. J. Peptide Protein Res. 23, 1984, 203–211).

Another, simpler method for preparing aminoethylglycine comprises the reductive amination of glyoxylic acid using ethylenediamine and is described in the application with the title "Process for preparing aminoethylglycine" (HOE 94/F 061, DE-P 44 08 530.3) which was submitted at the same time.

The nucleotide base-acetic acid derivatives of the formula VI are obtained by alkylating the corresponding nucleotide bases, or nucleotide bases which are protected in their exocyclic amino function, with chloroacetic acid, bromoacetic acid, iodoacetic acid or their esters. At the same time, temporary protecting groups are, where appropriate, additionally inserted on the nucleotide base for the selective alkylation. All protecting groups which are compatible with the base-labile protecting group PG may be used as a protecting group for the nucleotide bases. The protecting groups which are labile to weak acids and which are of the urethane type, such as Boc, Moz or DdZ, or of the trityl type, such as Trt, Mmt, Dmt or pixyl are preferably used for the exocyclic amino function. The protecting groups which are particularly preferred are those protecting groups which are labile to weak acids and which are of the trityl type, such as Trt, Mmt or Dmt, particularly preferably Mmt, with the latter surprisingly effecting a considerable improvement in the solubility of the monomeric structural components, so that solutions can be prepared for use in automatic synthesis equipment, such as, for example, multiple peptide synthesizers.

The nucleotide bases B', which are used in the preparation of the compounds of the formula V and which are protected in their exocyclic amino function, are prepared from the corresponding nucleotide bases by methods known per se from the literature using a suitable protecting group reagent such as, for example, Boc₂O, Moz-azide, Trt-Cl, Mtt-Cl, Mmt-Cl, Dmt-Cl or pixyl-Cl. Where appropriate, temporary protecting groups are additionally inserted at the same time on the nucleotide base for the selective alkylation.

The nucleotide base-acetic acids of the formula VI are coupled onto the aminoethylglycine derivatives of the formula V, which are protected with the base-labile protecting group, using activation methods, as described above, which are customary in peptide synthesis. The use of carbodiimides, for example dicyclohexylcarbodiimide or diisopropylcarbodiimide, is preferred. Phosphonium reagents, such as, for example, BOP (B. Castro, J. R. Dormoy, G. Evin and C. Selve, Tetrahedron Lett. 1975, 1219–1222) and uronium reagents, such as, for example, HBTU (V. Dourtoglou, B. Gross, V. Lambropoulou, C. Zioudrou, Synthesis 1984, 572–574); TBTU, TPTU, TSTU, TNTU (R. Knorr, A. Trzeciak, W. Bannwarth and D. Gillesson, Tetrahedron Letters 1989, 1927–1930); TOTU (EP-A-0 460 446), or acid chlorides or acid fluorides (L. A. Carpino, H. G. Chao, M. Beyermann and M. Bienert, J. Org. Chem., 56(1991), 2635; J.-N. Bertho, A. Loffet, C. Pinel, P. Reuther and G. Sennyey in E. Giralt and D. Andreu (Eds.) Peptides 1990, Escom Science Publishers B. V. 1991, pp. 53–54) are likewise preferably used.

The above-described PNAs are built up by solid phase synthesis on a suitable support material (e.g. polystyrene or polystyrene which is modified with polyoxyethylene, such as, for example, ®Tentagel or ®Controlled Pore Glass), which is provided with an anchor group L which contains the radical Q⁰ in a latent manner. The solid phase synthesis begins at the C-terminal end of the PNA with the coupling of a monomer which is protected with a base-labile protecting group, or an amino acid, which, where appropriate, is protected in its side chain function, to an appropriate resin.

After eliminating the base-labile protecting group of the structural component coupled to the resin using a suitable reagent as described above, the subsequent, protected structural components (PNA monomers and amino acid derivatives) are coupled on, one after the other, in the desired sequence. The PNA resins which arise as intermediates and which are protected at the N terminus with a base-labile protecting group are unblocked by the previously described reagents before they are linked to the subsequent PNA monomer.

The coupling or activation of the amino acid derivatives with one of the abovementioned activating reagents can be carried out in dimethylformamide, N-methylpyrrolidinone, acetonitrile or methylene chloride, or a mixture of the said solvents. The activated derivative is customarily employed in a 1.5 to 10 fold excess. In those cases in which incomplete coupling occurs, the coupling reaction is repeated without unblocking the amino group of the structural component which has just been coupled on.

Examples of methods for inserting the radical $R^0$, which are applicable when this radical contains a carboxylic acid function, are the above-described methods for coupling on the amino acids and PNA monomers. Other methods are the reaction of isocyanates, such as, for example, phenyl isocyanate, isothiocyanates, such as, for example, fluorescein isothiocyanate, chloroformic acid derivatives, such as, for example chloroformylcarbazole, active carbonates, such as, for example, cholesteryl-4-nitrophenyl carbonate or acridinium succinimidyl carbonate, sulfonyl chlorides, such as, for example, dansyl chloride, etc.

The previously described synthesis procedure may also be carried out using commercially available automated synthesizers, such as, for example, peptide synthesizers, multiple peptide synthesizers or DNA synthesizers if the synthesis programs which are normally used are slightly modified.

Once the PNAs have been synthesized in the previously described manner, the PNA oligomer can be cleaved from the resin using suitable reagents, such as, for example, trifluoroacetic acid in the case of anchor groups which are labile to weak or medium-strength acids. Depending on the nature of the linker and of the protecting groups which have been used, the oligomer and the additional side-chain protecting groups of the nucleotide bases are cleaved off simultaneously. Under these circumstances, the cleaving reagent can also be used diluted with suitable solvents, such as, for example, methylene chloride. Where appropriate, further additives may also be added to this cleaving reagent in order to avoid side reactions. Suitable cation-capturing agents in this context are substances such as phenol, cresol, thiocresol, anisole, thioanisole, ethanedithiol, dimethyl sulfide, ethyl methyl sulfide, triethylsilane, triisopropylsilane or similar additives which are customary in solid phase peptide synthesis, which additives can be added individually or as a mixture of two or more of these auxiliary substances.

Once it has been cleaved off, the crude oligomer which has been obtained is purified using methods, such as, for example, HPLC, ion exchange chromatography, etc., which are customary in peptide or nucleotide chemistry.

The abbreviations used for amino acids conform to the three letter code which is customary in peptide chemistry, as described in Europ. J. Biochem. 138, 9 (1984). Other abbreviations which are used are listed below.

| | |
|---|---|
| ACN | acetonitrile |
| Aeg | N-(2-aminoethyl)glycyl,-NH-CH$_2$-CH$_2$-NH-CH$_2$-CO- |
| Aeg(A$^{Mmt}$) | N-(2-aminoethyl)-N-((9-(N$^6$-4-methoxyphenyldiphenyl)adenosyl)acetyl)glycyl |
| Aeg(C$^{Mmt}$) | N-(2-aminoethyl)-N-((1-(N$^4$-4-methoxyphenyldiphenyl)cytosyl)acetyl)glycyl |
| Aeg(T) | N-(2-aminoethyl)-N-((1-thyminyl)acetyl)glycyl |
| Aeg(T$^{Bom}$) | N-(2-aminoethyl)-N-((1-(N$^3$-benzyloxymethyl)thyminyl)acetyl)glycyl |
| Aeg(T$^{triazolo}$) | N-(2-aminoethyl)-N-((2-hydroxy-5-methyl-4-triazolopyrimidin-1-yl)acetyl)glycyl |
| Bnpeoc | 2,2-[bis(4-nitrophenyl)]ethoxycarbonyl) |
| Boc | tert-butyloxycarbonyl |
| BOI | 2-(benzotriazol-1-yl)oxy-1,3-dimethyl-imidazolidinium hexafluorophosphate |
| Bom | benzyloxymethyl |
| BOP | benzotriazol-1-yloxytris(dimethylamino)-phosphonium hexafluorophosphate |

-continued

| | |
|---|---|
| BroP | bromotris(dimethylamino)phosphonium hexafluorophosphate |
| BSA | N,O-bis(trimethylsilyl)acetamide |
| But | tert-butyl |
| Bzl | benzyl |
| Cl-Z | 4-chlorobenzyloxycarbonyl |
| CPG | Controlled Pore Glass |
| DBU | 1,8-diazabicyclo[5.4.0]undec-7-ene |
| DCM | dichloromethane |
| Dde | 1-(4,4-dimethyl-2,6-dioxocyclohexyl-idene)ethyl |
| Ddz | 3,5-dimethoxyphenyl-2-propyl-2-oxycarbonyl |
| DMF | dimethylformamide |
| DMT | 4,4'-dimethoxytriphenylmethyl |
| Dmt | di-(4-methoxyphenyl)phenylmethyl, |
| Dnpeoc | 2-(2,4-dinitrophenyl)ethoxycarbonyl |
| FAM | fluorescein residue |
| Fmoc | 9-fluorenylmethyloxycarbonyl |
| H-Aeg-OH | N-(2-aminoethyl)glycine |
| HAPyU | O-(7-azabenzotriazol-1-yl)-1,1,3,3-bis-(tetramethylene)uronium hexafluorophosphate |
| HATU | O-(7-azabenzotriazol-1-yl)-1,1,3,3-tetramethyluronium hexafluorophosphate |
| HBTU | O-(benzotriazol-1-yl)-1,1,3,3-tetramethyluronium hexafluorophosphate |
| HOBt | 1-hydroxybenzotriazole |
| HONSu | N-hydroxysuccinimide |
| HOObt | 3-hydroxy-4-oxo-3,4-dihydrobenzotriazine |
| MeOBz | 4-methoxybenzoyl |
| Mmt | 4-methoxytriphenylmethyl |
| Moz | 4-methoxybenzyloxycarbonyl |
| MSNT | 2,4,6-mesitylenesulfonyl-3-nitro-1,2,4-triazolide |
| Mtt | 4-(methylphenyl)diphenylmethyl |
| NBA | nitrobenzyl alcohol |
| NMP | N-methylpyrrolidine |
| Pixyl | 9-(9-phenyl)xanthenyl |
| PyBOP | benzotriazolyl-1-oxytripyrrolidinophos-phonium hexafluorophosphate |
| PyBroP | bromotripyrrolidinophosphonium hexafluorophosphate |
| TAPipU | O-(7-azabenzotriazol-1-yl)-1,1,3,3-bis-(pentamethylene)uronium tetrafluoroborate |
| TBTU | O-(benzotriazol-1-yl)-1,1,3,3-tetramethyluronium tetrafluoroborate |
| tBu | tert-butyl |
| tBuBz | 4-tert-butylbenzoyl |
| TDBTU | O-(3,4-dihydro-4-oxo-1,2,3-benzotriazin-3-yl)-1,1,3,3-tetramethyluronium tetrafluoroborate |
| TDO | 2,5-diphenyl-2,3-dihydro-3-oxo-4-hydroxy-thiophene dioxide |
| TFA | trifluoroacetic acid |
| THF | tetrahydrofuran |
| TNTU | O-(5-norbornene-2,3-dicarboximido)-1,1,3,3-tetramethyluronium tetrafluoroborate |
| TOTU | O-[(cyano(ethoxycarbonyl)methylene)-amino]-1,1,3,3-tetramethyluronium tetrafluoroborate |
| TPTU | O-(1,2-dihydro-2-oxo-1-pyridyl)-1,1,3,3'-tetramethyluronium tetrafluoroborate |
| Trt | trityl |
| TSTU | O-(N-succinimidyl)-1,1,3,3-tetramethyl-uronium tetrafluoroborate |
| Z | benzyloxycarbonyl |
| MS(ES$^+$) | electrostatic spray mass spectrum (positive ion) |
| MS(ES$^-$) | electrostatic spray mass spectrum (negative ion) |
| MS(DCI) | desorption chemical ionization mass spectrum |
| MS(FAB) | fast atom bombardment mass spectrum |

The following examples are intended to elucidate the preferred methods for preparing the compounds according to the invention without the invention being restricted thereto.

EXAMPLE 1

N-(Fmoc-aminoethyl)glycine methyl ester hydrochloride

Fmoc-Aeg-Oxe.HCl 8.2 g of aminoethylglycine methyl ester dihydrochloride are dissolved in 100 ml of water, and 13.48 g of Fmoc-ONSu in 400 ml of dioxane are added while stirring vigorously. 10.08 g of sodium hydrogen carbonate in 150 ml of water are then added dropwise within the space of 15 min. The mixture is left to stir at room temperature for a further 15 h and is then concentrated in vacuo down to about 100 ml. This concentrated mixture is extracted with 600 ml of ethyl acetate and the organic phase is washed 3 times with 50 ml of water on each occasion. The organic phase is dried over sodium sulfate and is then concentrated to a volume or approximately 50 ml. 100 ml of dichloromethane and 20 ml of 2N methanolic hydrochloric acid are added, whereupon the product precipitates out immediately. The mixture is allowed to stand at 4° C. overnight in a closed flask. The precipitate is filtered off with suction and dried.

Yield: 9.8 g
RF: 0.50 (n-butanol/acetic acid/water 3:1:1)
MS(FAB, NBA/LiCl): 361.2 [M+Li]$^+$

EXAMPLE 2

N-(Fmoc-aminoethyl)glycine hydrochloride

Fmoc-Aeg-OH.HCl 11.21 g of aminoethylglycine are suspended in 250 ml of DMF, and 98.8 ml of bis(trimethylsilyl)acetamide are added while stirring. After 15 min of stirring, a clear solution is obtained. A solution of 33.7 g of Fmoc-ONSu in 200 ml of DMF is added dropwise to it within the space of 15 min. This reaction mixture is subsequently stirred for a further 1 h and 100 ml each of methanol and water are then added to it. After 10 min, 16.6 ml of 6N hydrochloric acid are also added and the mixture is stirred for a further 10 min. After that, the mixture is concentrated to dryness in vacuo on a rotary evaporator, and 250 ml of dichloromethane are added to the residue and this mixture is stirred. This results initially in a clear solution, from which the product then slowly precipitates out after about 5 min. A further 250 ml of dichloromethane are gradually added and the mixture is stirred for a total of 1.5 h. The precipitated product is rapidly filtered off with suction and then stirred up twice, on the suction filter, with 150 ml of dichloromethane on each occasion, and filtered off with suction. The precipitate is subsequently transferred to a flask and thoroughly stirred, at 45° C., with approximately 300 ml of ethyl acetate, the precipitate is filtered off from the warm solution and then washed with a little warm ethyl acetate. The precipitate is thoroughly dried in a vacuum desiccator.

Yield: 34.4 g

EXAMPLE 3

Liberation of Fmoc-aminoethylglycine

Fmoc-Aeg-OH 23 g of the above Fmoc-aminoethylglycine hydrochloride are dissolved in 400 ml of hot methanol. After the mixture has been cooled down to room temperature, a solution of 2.2 g of NaOH in 80 ml of methanol is added dropwise while stirring thoroughly. The product then precipitates out immediately. 40 ml of water are now added to the solution and this mixture is heated, resulting in a clear solution which is allowed to cool down slowly to room temperature and then left to stand for a further 1 h at 0° C. The precipitate is filtered off with suction, washed three times with 70 ml of 90 % aqueous methanol on each occasion and then dried well in a vacuum desiccator.

Yield: 15.0 g
$R_F$: 0.55 (n-butanol/acetic acid/water 2:1:2)
MS(FAB, NBA): 341.2 [M+H]$^+$

EXAMPLE 4

Methyl 2-amino-6-chloropurin-9-ylacetate 1.43 g of sodium hydride (95%) are initially introduced, under an argon atmosphere, into a well-dried glass apparatus, and 200 ml of well-dried N,N-dimethylformamide are poured over the hydride. 10.0 g of 2-amino-6-chloropurine are then added, resulting in the evolution of gas and heat and the formation of a yellow solution. After this solution has been thoroughly stirred for one hour, a solution of 10.8 g of methyl bromoacetate in 40 ml of DMF is added dropwise to it. The reaction mixture is left to stir for a further 2 h and is then concentrated on a rotary evaporator under an oil pump vacuum. Water is added to the residue and this mixture is then extracted with ethyl acetate. The organic phase is concentrated to dryness and the crude product is purified by means of flash chromatography on silica gel using dichloromethane/methanol (95/5).

Yield: 11 g of product
$R_F$: 0.44 (dichloromethane/methanol 9:1)
MS(CI): 242(M+H)$^+$

EXAMPLE 5

Methyl 2-(4-methoxyphenyldiphenylmethylamino)-6-chloropurin-9-ylacetate 11 g of methyl 2-amino-6-chloropurin-9-ylacetate are suspended, under argon, in a mixture of 75 ml of pyridine and 9.5 ml of triethylamine, and 15 g of 4-methoxyphenyldiphenylmethyl chloride are then added, in 4 portions, within the space of one hour. The mixture is left to react overnight and is then concentrated to dryness; the residue is coevaporated once with a little toluene, and the crude product is purified by means of flash chromatography on silica gel using dichloromethane/methanol (98:2).

Yield: 15.5 g
$R_F$: 0.60 (dichlorometainel/methanol 97:3)
MS (ES$^+$): 514.2(M+H)$^+$

EXAMPLE 6

2-(4-Methoxyphenyldiphenylmethylamino)-6-hydroxypurin-9-ylacetic acid 0.5 g of methyl 2-(4-methoxyphenyldiphenylmethylamino)-6-chloropurin-9-ylacetate are heated for 3 h, under reflux, in 12 ml of a 10% solution of sodium hydroxide. The mixture is then allowed to cool down to room temperature and carefully neutralized with 10% HCl. The precipitated product is filtered off with auction, washed several times with water and dried well.

Yield: 400 mg
$R_F$: 0.1 (dichloromethane/methanol 7:3)
MS(FAB, NBA/LiCl): 488.2(M+Li)$^+$

EXAMPLE 7

6-(4-Methoxyphenyldiphenylmethylamino)purine 13.5 g of 6-aminopurine and 46.2 g of 4-methoxyphenyldiphenylmetbyl chloride are suspended in 500 ml of dry dimethylformamide, and, after adding 13.9 ml of triethylamine, this mixture is heated briefly at 60° C. The virtually clear, greenish solution is left to stand overnight. The mixture is then concentrated on a rotary evaporator in vacuo and, following the addition of 50 ml of methanol, concentrated once more. The residue is purified chromatographically on silica gel using dichloromethane/methanol (95:5), with this mixture containing 0.1% triethylamine.

Yield: 9.8 g of a foam $R_F$: 0.35 (dichloromethane/methanol 9:1)

MS(FAB, MeOH/NBA): 408.2(M+H)$^+$

EXAMPLE 8

6-(4-Methoxyphenyldiphenylmethylamino)purine 20.25 g of 6-aminopurine and 69.3 g of 4-methoxyphenyldiphenylmethyl chloride are suspended in 500 ml of dry pyridine, and, following addition of 19.1 ml of 4-ethylmorpholine, the mixture is heated briefly at approximately 40° C. The mixture is left to stand overnight. The suspension is then stirred up with water and dichloromethane, and the precipitate is filtered off with suction. The dichloromethane phase is concentrated to dryness in vacuo and triturated with a little dichloromethane; the precipitate is filtered off with suction and combined with the precipitate which was first obtained. After drying, 47.3 g of product are obtained.

$R_F$: 0.53 (ethyl acetate)

MS(FAB, MeOH/NBA): 408.2(M+H)$^+$

EXAMPLE 9

Methyl 6-(4-methoxyphenyldiphenylmethylamino) purin-9-ylacetate 6.2 g of 6-(4-methoxyphenyldiphenylmethylamino) purine are dispersed in 75 ml of dry dimethylformamide, and 0.36 g of sodium hydride is then added. The mixture is subsequently stirred for one hour, and 2.52 g of methyl bromoacetate are then added and stirring is continued for a further 2 h. 2 ml of methanol are then added to the reaction mixture, which is subsequently stirred for 10 min and then concentrated on a rotary evaporator in vacuo. The residue is purified by chromatography on silica gel using ethyl acetate containing 0.5% triethylamine.

Yield: 4.0 g of a foam $R_F$: 0.68 (ethyl acetate/methanol 3:1)

MS(FAB, NBA/LiCl): 480.2(M+H)$^+$; 485.2(M+Li)$^+$

EXAMPLE 10

6-(4-Methoxyphenyldiphenylmethylamino)purin-9-ylacetic acid 3.0 g of methyl 6-(4-methoxyphenyldiphenylmethylamino)purin-9-ylacetate are dissolved in 20 ml of dimethylformamide, and 0.25 g of NaOH in 5 ml of water is added to this solution, while stirring. After 10 min, the hydrolysis is complete and the reaction mixture is adjusted to pH 6 using dilute acetic acid. The mixture is further diluted with 100 ml of water and is then concentrated in vacuo on a rotary evaporator. The residue is subsequently distilled twice with a little toluene; diethyl ether is added to the residue thus obtained, whereupon the product crystallizes out. The precipitated product is filtered off with suction then washed with a little diethyl ether and dried.

Yield: 3.2 g

Melting point: 157–160° C. (decomp.)

$R_F$: 0.15 (ethyl acetate/methanol 3:1)

MS(FAB, NBA/LiCl); 465.1(M+H)$^+$; 472.1(M+Li)$^+$; 478.2(M+2Li)$^+$

EXAMPLE 11

1-Acetyl-2,4-dihydroxy-5-methylpyrimidine

1-Acetylthymine 75 g of thymine are suspended in 375 ml of acetic anhydride, and this suspension is heated under reflux for 45 min. After that, the mixture is cooled down to 0° C., whereupon the product precipitates out. The precipitate is filtered off with suction and stirred up with 375 ml of ethyl acetate. The precipitate is filtered off with suction, then washed with a little diethyl ether and dried.

Yield: 89.1 g

Melting point: 187–189° C.

$R_F$: 0.67 (dichloromethane/methanol 95:5)

EXAMPLE 12

3-Benzyloxymethyl-2,4-dihydroxy-5-methylpyrimidine

3-Benzyloxymethylthymine 52.0 g of 1-acetyl-2,4-dihydroxy-5-methylpyrimidine are suspended in 300 ml of DMF, and, following addition of 47.5 ml of triethylamine, the mixture is cooled down to 0° C. 100 ml of benzyl chloromethyl ether in 50 ml of DMF are slowly added dropwise, at this temperature, to the mixture which has been thoroughly stirred. The mixture is subsequently stirred for a further 1 h and then left to stand at room temperature overnight. The reaction mixture is then concentrated in vacuo on a rotary evaporator, and the residue is taken up in 450 ml of methanol and 300 ml of a 40% aqueous solution of methylamine; this mixture is boiled at reflux for 1.5 h. The solution is then concentrated and the residue is stirred up with 10.8 g of sodium hydrogen carbonate in 600 ml of water. The precipitated product is filtered off with suction, washed with water and ethanol, and recrystallized from ethanol.

Yield: 46.66 g

Melting point: 119–120° C.

$R_F$: 0.38 (dichloromethane/methanol 95:5)

EXAMPLE 13

Ethyl 3-benzyloxymethyl-2,4-dihydroxy-5-methylpyrimidineacetate

Ethyl 3-benzyloxymethylthyminylacetate 4.97 g of sodium hydride are initially introduced in 150 ml of THF, 45.04 g of 3-benzyloxymethyl-2,4-di-hydroxy-5-methylpyrimidine, dissolved in 550 ml of THF, are then added dropwise, under a $N_2$ atmosphere and at 0° C., and, following that, 21.42 ml of ethyl bromoacetate in 700 ml of THF are added at this temperature. After that, the mixture is left to stir at room temperature for a further 5 h, and water is then carefully added. The organic phase is separated off and the water phase is extracted a further four times with dichloromethane. The combined organic phases are dried over magnesium sulfate and concentrated, and the residue is stirred up with heptane.

Yield: 52.4 g
$R_F$: 0.15 (dichloromethane/methanol 95:5)
MS(FAB, NBA): 319.1(M+H)$^+$

EXAMPLE 14

Ethyl 2,4-dihydroxy-5-methylpyrimidineacetate

Ethyl thyminylacetate 25 g of ethyl 3-benzyloxymethyl-2,4-dihydroxy-5-methylpyrimidineacetate are dissolved in 1000 ml of dichloromethane, the mixture is cooled down to −70° C., and 375 ml of a 1M solution of boron trichloride in dichloromethane are added dropwise to the mixture, at this temperature and while stirring thoroughly. The mixture is left to continue reacting at this temperature for a further 3 h, and 320 ml of methanol are then added dropwise at from −70° to −60° C. After 1 h, 197.05 ml of triethylamine are added and the mixture is allowed to come to room temperature. Some water is then added and the mixture is concentrated on a rotary evaporator. The residue is taken up in ethyl acetate and this mixture is washed with water. The organic phase is dried over magnesium sulfate and then concentrated to dryness.

Yield: 12 g
$R_F$: 0.45 (dichloromethane/methanol 9:1)
MS(DCI): 199(M+H)$^+$

EXAMPLE 15

2,4-Dihydroxy-5-methylpyrimidineacetic acid Thyminylacetic acid 10 g of ethyl 2,4-dihydroxy-5-methylpyrimidineacetate are dissolved in 130 ml of dioxane/water (1:1) and then, after 60 ml of 1N LiOH have been added, the mixture is stirred at room temperature overnight. It is then concentrated to a small Volume and the aqueous phase is washed with ether and then adjusted to pH 2.5. At this point, the product precipitates out. It is filtered of f with suction, resulting in 4.9 g of product. A further 1.5 g of product can be obtained from the mother liquor by extracting with pentanol and precipitating with heptane/ether.

Yield: 6.4 g
$R_F$: 0.30 (dichloromethane/methanol 3:2)
MS(DCI): 185(M+H)$^+$

EXAMPLE 16

$N_1$-chlorocarboxymethylthymine

Thyminylacetyl chloride

EXAMPLE 16a 2 g of 2,4-dihydroxy-5-methylpyrimidineacetic acid are stirred, at 60° C. for 3 h, with 15 ml of thionyl chloride until there is no further evolution of gas. The excess thionyl chloride is then stripped off in vacuo on a rotary evaporator, and the residue is subsequently distilled three times with a little toluene. The resulting product is used directly in the subsequent reaction.

Yield: 2.4 g
MS(DCI): 203 (M+H)$^+$

EXAMPLE 16b $N^1$-carboxymethylthymine (3.0 g; 16.3 mmol) is suspended in thionyl chloride (90 ml). The suspension is heated at 70° C. for 1.5 h and then left to stand at room temperature for 16 h. The excess thionyl chloride is removed in vacuo and the residue is coevaporated three times together with toluene. The resulting product is triturated twice with n-hexane and dried in vacuo. The compound is obtained as a pale orange powder.

Yield: 3.30 g
MS(CI; dichloromethane); 203(M+H)$^+$
$R_f$=0.10 (dichloromethane/methanol 7:3).

EXAMPLE 17

2-Hydroxy-4-(4-methoxyphenyldiphenylmethylamino)pyrimidine $N^4$-Mmt-cytosine 11.6 g of 4-amino-2-hydroxypyrimidine and 46.2 g of 4-methoxyphenyldiphenylmethyl chloride are suspended in 500 ml of dry pyridine and, after the addition of 12.8 ml of 4-ethylmorpholine, this mixture is briefly heated at approximately 40° C. It is left to stand overnight. The suspension is then stirred up with water and dichloromethane and the precipitate is filtered off with suction. The dichloromethane phase is concentrated to dryness in vacuo and the residue triturated with a little dichloromethane; the precipitate is filtered off with suction and combined with the first precipitate to be obtained. After drying, 16.8 g of product are obtained.

$R_F$: 0.45 (dichloromethane/methanol 9:1)
MS(FAB,MeOH/NBA): 384.2(M+H)$^+$

EXAMPLE 18

Methyl 2-hydroxy-4-(4-methoxyphenyldiphenylmethylamino)-pyrimidin-1-ylacetate

Methyl $N^4$-Mmt-cytosylacetate 11.5 g of 2-hydroxy-4-(4-methoxyphenyldiphenylmethylamino)pyrimidine are dispersed in 120 ml of dry dimethylformamide, and 0.72 g of sodium hydride are then added. The mixture in subsequently stirred for one hour and 5.05 g of methyl bromoacetate are then added and stirring is continued for a further 2 h. 2 ml of methanol are then added to the reaction mixture, which is subsequently stirred for 10 min and then concentrated in vacuo on a rotary evaporator. The residue is triturated with water, filtered off with suction and dried.

Yield: 10.7 g
$R_F$: 0.39 (ethyl acetate)
MS(FAB, NBA/LiCl): 462.2(M+Li)$^+$

EXAMPLE 19

2-Hydroxy-4-(4-methoxyphenyldiphenylmethylamino)pyrimidin-1-ylacetic acid $N^4$-Mmt-cytosylacetic acid 10.5 g of methyl 2-hydroxy-4-(4-methoxyphenyldiphenylmethylamino)pyrimidin-1-ylacetate are dissolved in 100 ml of dimethylformamide, and 0.94 g of NaOH in 5 ml of water is added to this mixture, while stirring. After 10 min. the hydrolysis is complete and the reaction mixture is adjusted to pH 6 using dilute acetic acid. It is subsequently diluted with 100 ml of water and then concentrated in vacuo on a rotary evaporator. The residue is subsequently distilled twice with a little toluene, and diethyl ether is added to the residue from these distillations, whereupon the product precipitates out. The precipitated product is filtered off with suction, then washed with a little diethyl ether and dried.

Yield: 8.55 g $R_F$: 0.27 (ethyl acetate)

MS(FAB, NBA/LiCl): 448(M+Li)$^+$

EXAMPLE 20

$N^4$-(tert-Butyloxycarbonyl)-$N^1$-carboxymethylcytosine $N^4$-Boc-cytosylacetic acid

EXAMPLE 20a $N^4$-(tert-Butyloxycarbonyl)cytosine $N^4$-Boc-cytosine

Cytosine (11.1 g) is suspended in dry pyridine (250 ml). Di-tert-butyl dicarbonate (21.8 g) and a spatula tip of 4-dimethylaminopyridine are then added. The mixture is stirred at 60° C. for 6 h, resulting in the appearance of a thick precipitate. The reaction solution is cooled down and the precipitate is filtered off with suction. The precipitate is stirred up with warm water, filtered off with suction and dried in vacuo.

Yield: 10.26 g

MS(DCI): 212(M+H)$^+$.

$R_F$: 0.6 (dichloromethane/methanol 6:4)

EXAMPLE 20b $N^4$-(tert-Butyloxycarbonyl)-$N^1$-methoxycarbonylmethylcytosine Methyl $N^4$-Boc-cytosylacetate $N^4$-(tert-Butyloxycarbonyl)cytosine (1. 6 g) is suspended in dry DMP (30 ml), sodium hydride (0.19 g) is added in portions, and the mixture is stirred at room temperature for 1.5 h until the evolution of hydrogen is complete. Methyl bromoacetate (0.84 ml) is subsequently added dropwise, at room temperature, using a syringe. The mixture is stirred at room temperature for a further 5 h and methanol (1 ml) is then added. The solvent is stripped off in vacua and the remaining residue is purified by means of column chromatography on silica gel using dichloromethane as eluent. The fractions containing the product are combined and concentrated in vacua.

Yield: 1.1 g

MS(DCI): 284(M+H)$^+$.

$R_F$: 0.5 (dichloromethane/methanol 95:5)

EXAMPLE 20c $N^4$-(tert-Butyloxycarbonyl)-$N^1$-carboxymethylcytosine

N 4-(Boc-cytosylacetic acid)

N -(tert-Butyloxycarbonyl)-$N^1$-methoxycarbonylmethylcytosine (4.2 g) is suspended in water (30 ml), and 2N aqueous sodium hydroxide solution is added dropwise, at 0° C. and while controlling the pH (pH 12), until the methyl ester is hydrolyzed. The progress of the reaction is monitored by means of TLC. The reaction solution is then adjusted to pH 3 with acetic acid and the solvent is distilled off in vacuo. The crude product is purified by means of column chromatography on silica gel using dichloromethane/methanol/triethylamine 8:1:1 as eluent. The fractions containing the product are combined and concentrated in vacuo.

Yield: 3.5 g

Melting point: 95–98° C., decomp.

MS(FAB,NBA): 270.2(M+H)$^+$.

$R_F$: 0.35 (dichloromethane/methanol/triethylamine 8:1:1)

EXAMPLE 21

N-[2-(4-Methoxyphenyldiphenylmethylamino)-6-hydroxypurin-9-ylacetyl]-N-2-(9-fluorenylmethyloxycarbonylamino) ethylglycine Fmoc-Aeg ($G^{Mmt}$)-OH 1 g of 2-(4-methoxyphenyldiphenylmethylamino)-6-hydroxypurin-9-ylacatic acid is dissolved in DMF, and 682 mg of TOTU and 239 mg of N-ethylmorpholine are added, one after the other, to the solution, which has been cooled down to 0° C. The mixture is subsequently stirred at room temperature for 20 min. A solution of 1.06 g of Fmoc-aminoethylglycine in 4 ml of dimethylformamide and 1.5 g of bis(trimethylsilyl)acetamide is prepared in a separate flask. This solution is then added to the preactivated solution of 2-(4-methoxyphonyldiphenylmethylamino)-6-hydroxypurin-9-ylacetic acid. The mixture is stirred for a further 2 h and then concentrated to dryness. After that, the residue is taken up in 30 ml of ethyl acetate and this mixture is extracted three times with 15 ml of water on each occasion. The organic phase is dried over sodium sulfate and purified chromatographically on silica gel using methanol/dichloromethane/water/glacial acetic acid (1.5:10:0.25:0.075).

Yield: 600 mg $R_F$: 0.35 (methylene chloride: methanol/7:3)

MS(FAB, DMSO/NBA/LiCl): 810.3(M+Li)$^+$

EXAMPLE 22

N-[6-(4-Methoxyphenyldiphenylmethylamino)purin-9-yl-acetyl]-N-2-(9-fluorenylmethyloxycarbonylamino)ethylglycine methyl ester Fmoc-Aeg($A^{Mmt}$)-OMe A mixture of 848 mg (2.6 mmol) of Fmoc-Aeg-OMe. HCl and 407 mg (2.5 mmol) of HOOBt is dissolved in 5 ml of DMF, and 640 µl (5 mmol) of NEM and 1.2 g (2.5 mmol) of 6-(4-methoxyphenyldiphenylmethylamino)purin-9-ylacetic acid, dissolved in 5 ml of DMF, are then added to this solution. After that, 471 µl (3 mmol) of diisopropylcarbodiimide are added and the mixture is stirred at room temperature for 4 h. The mixture is then filtered and the filtrate is concentrated on a rotary evaporator in vacuo. The amorphous residue is taken up in dichloromethane and this mixture is extracted with water and a solution of sodium hydrogen carbonate; the organic phase is dried over sodium sulfate and then concentrated to dryness in vacuo. The residue is dissolved in 4.5 ml of ethyl acetate and precipitation is effected by adding 20 ml of diisopropyl ether. The resulting semi-solid precipitate is dissolved in 20 ml of methanol, precipitated by adding 30 ml of water and then dried in vacuo.

Yield: 1.05 g
$R_F$: 0.85 (n-butanol/acetic acid/water 3:1:1)
NS(FAB, DMSO/NBA): 802.4(M+H)$^+$

EXAMPLE 23

Synthesis of N-[6-(4-methoxyphenyldiphenylmethylamino)-purin-9-ylacetyl]-N-2-(9-fluorenylmethyloxycarbonylamino) ethylglycine Fmoc-Aeg (A$^{Mmt}$)-OH 900 mg (1.125 mmol) of Fmoc-Aeg(A$^{Mmt}$)-OMe are dissolved in a mixture of 5 ml of dioxane and 2.5 ml of water and hydrolyzed, while cooling with ice water, by the portion-wise addition of a mixture of 2.4 ml of 1N NaOH and 2.5 ml of dioxane. Once the reaction is complete, the mixture is buffered by adding a little solid carbon dioxide and the elimination of Fmoc, which has taken place to a small extent, is reversed by adding Fmoc-ONSU. Most of the dioxane is then distilled off in vacuo and the solution is diluted with water and overlaid with ethyl acetate/n-butanol (1:1). The mixture is acidified to pH 5 to 6 by adding a solution of potassium hydrogen sulfate, while cooling with ice water. The organic phase is separated off and the aqueous phase in extracted a further two times with ethyl acetate/butanol (1:1). The combined organic phases are dried over sodium sulfate and concentrated in vacuo on a rotary evaporator. The residue is dissolved in 5 ml of ethyl acetate and precipitated by adding 20 ml of methyl butyl ether.

Yield: 1.02 g
$R_F$: 0.73 (n-butanol/acetic acid/water 3:1:1)
MS(FAB, DMSO/NBA): 787(M+H)$^+$, 794(M+Li)$^+$

EXAMPLE 24

N-(2,4-Dihydroxy-5-methylpyrimidin-1-ylacetyl)-N-2-(9-fluorenylmethyloxycarbonylamino)ethylglycine Fmoc-Aeg (T)-OH 4.03 g of Fmoc-Aeg-OH are suspended in 80 ml of DMF, 4.39 ml of N,O-bis(trimethylsilyl)acetamide are added, and the mixture is stirred at room temperature for 40 min. 2.4 g of 2,4-dihydroxy-S-methylpyrimidinaleatyl chloride are then added, at 0° C. and while stirring thoroughly, to the clear solution. The mixture is left to react at room temperature for a further 3 h and the solvent is then distilled of f on a rotary evaporator. Water is added to the resulting crude product and this mixture is left to stand at 0° C. overnight. The water is then decanted off and the residue is dried under high vacuum and purified chromatographically on silica gel using dichloromethane/methanol/glacial acetic acid/water (500/100/25/2). The combined product fractions are concentrated to dryness and subsequently distilled a further three times with a little toluene.

Yield: 3.8 g
$R_F$: 0.42 (dichloromethane/methanol/acetic acid 100:20:5)
MS(FAB, DMSO/NBA): 507.3(M+H)$^+$

EXAMPLE 25

N-(2,4-Dihydroxy-5-methylpyrimidin-1-ylacetyl)-N-2-(9-fluorenylmethyloxycarbonylamino)ethylglycine Fmoc-Aeg(T)-OH A mixture of 386 mg (2 mmol) of 2,4-dihydroxy-5-methylpyrimidineacetic acid and 652 mg (4 mmol) of HOOBt is briefly heated at from 70 to 8° C. in 6 ml of dry DMF. After the mixture has been cooled down to room temperature, 314 µl (2 mmol) of diisopropylcarbodiimide are added and the mixture is stirred for 30 min. After that, 680 mg (2 mmol) of Fmoc-Aeg-OH are added. At intervals of 30 min, the mixture is briefly heated three times at approximately 70° C. The solvent is then evaporated off in vacuo on a rotary evaporator and the remaining residue is triturated with water; the resulting crude product is partitioned between n-butanol and water. The organic phase is extracted with a solution of potassium hydrogen sulfate, with a solution of potassium hydrogen carbonate and with water. The organic phase is then concentrated in vacuo on a rotary evaporator, whereupon the product precipitates out.

Yield: 260 mg
$R_F$: 0.40 (n-butanol/acetic acid/water 3:1:1)
MS(FAB, DMSO/NBA): 507.3(M+H)$^+$

EXAMPLE 26

N-[2-Hydroxy-4-(4-methoxyphenyldiphenylmethylamino)pyrimidin-1-ylacetyl]-N-2-(9-fluorenylmethyloxycarbonylamino)-ethylglycine methyl ester Fmoc-Aeg (C$^{Mmt}$)-OMe A mixture of 1.7 g (5 mmol) of Fmoc-Aeg-OMe.HCl and 675 mg (5 mmol) of HOOBt is dissolved in 10 ml of dried DMF, and 1.28 ml (10 mmol) of NEM are added. The mixture is then cooled to 0° C. and 2.21 g (5 mmol) of 2-hydroxy-4-(4-methoxyphenyldiphenylmethylamino) pyrimidin-1-ylacetic acid are added, followed by 5 mmol of diisoprgpylcarbodiimide; this mixture is then stirred at 0° C. for 30 min. It is subsequently stirred at room temperature for 4.5 h and the solvent is then distilled off in vacuo on a rotary evaporator. The residue is partitioned between dichloromethane and water, and the organic phase is washed with a solution of sodium hydrogen carbonate and with water, dried over sodium sulfate and concentrated to dryness in vacuo on a rotary evaporator. The residue is dissolved in 10 ml of methanol and precipitated out by adding 15 ml of water. The resulting product is triturated with a little water and dried over potassium hydroxide in a vacuum desiccator.

Yield; 3.19 g
$R_F$: 0.79 (n-butanol/pyridine/water/acetic acid 8:2:2:10)
MS(FAB, DMBO/NBA): 778.4(M)$^+$

EXAMPLE 27

N-[2-Hydroxy-4-(4-methoxyphenyldiphenylmethylamino)pyrimidin-1-ylacetyl]-N-2-(9-fluorenylmethyloxycarbonylamino)-ethylglycine Fmoc-Aeg (C$^{Mmt}$)-OH 3.0 g (3.86 mmol) of Fmoc-Aeg(C$^{Mmt}$)-OMe are dissolved in a mixture of 15 ml of dioxane and 10 ml of water and hydrolyzed, while the solution is being cooled with ice water, by the portion-wise addition of 10.2 ml of a mixture of 1N NaOH and dioxane (1:1). After the reaction is complete, the mixture is buffered by adding a little solid carbon dioxide, and the Fmoc elimination, which has taken place to a small extent, is reversed by adding 0.5 g of Fmoc-ONSU and subsequently stirring for 45 minutes. The mixture is then adjusted to pH 6.5 with 0.5 ml of a 2M solution of potassium hydrogen sulfate. Most of the dioxane is subsequently distilled off in vacuo and the solution is diluted with water and overlaid with ethyl acetate. The mixture is acidified to pH 5, while being cooled with ice water, by adding a solution of potassium hydrogen sulfate. The organic phase is separated off and the aqueous phase is extracted a further two times with ethyl acetate. The combined organic phases are dried over sodium sulfate and concentrated in vacuo on a rotary evaporator. The residue is dissolved in a mixture of 5 ml of methanol and 15 ml of ethyl acetate and precipitated out by adding 80 ml of methyl butyl ether. The product is filtered off and dried in vacuo.

Yield: 1.95 g $R_F$: 0.80 (n-butanol/acetic acid/water 3:1:1)

MS(FAB, DMSO/NBA/LiCl): 770.3 $(M+Li)^+$

EXAMPLE 28

N-[2-Hydroxy-4-(tert-butyloxycarbonylamino) pyrimidin-1-ylacetyl]-N-2-(9-fluorenylmethyloxycarbonylamino)ethylglycine methyl aster Fmoc-Aeg($C^{Boc}$)-OMe A mixture of 0.8 g (3 mmol) of $N^4$-(tert-butyloxycarbonyl)-$N^1$-carboxymethylcytosine and 0.49 g (3 mmol) of HOOBt is dissolved in 5 ml of dry DMF, and then 766 μl (6 mmol) of NEM are added, followed by 1.02 g (3 mmol) of Fmoc-Aeg-OMe.HCl. The mixture is then cooled to 0° C., 564 μl (3.6 mmol) of diisopropylcarbodiimide are added, and the mixture is stirred at 0° C. for 30 min and at room temperature for 4 h. The solvent is then distilled off in vacuo on a rotary evaporator. The residue is partitioned between dichloromethane and water, and the organic phase is washed with a solution of sodium hydrogen carbonate and with water, dried over sodium sulfate and concentrated to dryness in vacuo on a rotary evaporator. The residue is recrystallized from 20 ml of ethyl acetate.

Yield: 1.19 g $R_F$: 0.88 (n-butanol/acatic acid/water 3:1:1)

MS(FAB, DMSO/NBA): 606.3 $(M^+)$

EXAMPLE 29

Fmoc-Aeg($C^{Boc}$)-OMe

A mixture of 2.87 g (8.47 mmol) of Fmoc-Aeg-OMe.HCl and 1.38 g (8.47 mmol) of HOOBt is dissolved in 15 ml of dry DMF, and then 1.08 ml (8.47 mmol) of NEM are added, followed by 2.4 g (8.47 mmol) of $N^4$-(tert-butyloxycarbonyl)-$N^1$-carboxymethylcytosine. The mixture is then cooled to 0° C. and 1.33 ml (8.47 mmol) of diisopropylcarbodiimide are added; this mixture is stirred at 0° C. for 30 min and at room temperature for 3 h. The solvent is then distilled off in vacuo on a rotary evaporator. The residue is taken up in 100 ml of dichloromethane and the organic phase is washed consecutively with water, a solution of sodium hydrogen carbonate, and water, dried over sodium sulfate and concentrated to dryness in vacuo on a rotary evaporator. The residue is triturated with methyl tert-butyl ether.

Yield: 4.5 g $R_F$: 0.88 (n-butanol/acetic acid/water 3:1:1)

EXAMPLE 30

N-[2-Hydroxy-4-(tert-butyloxycarbonylamino) pyrimidin-1-ylacetyl]-N-2-(9-fluorenylmethyloxycarbonylamino) ethylglycine Fmoc-Aeg ($C^{Boc}$)-OH 700 mg (1.15 mmol) of Fmoc-Aeg($C^{Boc}$)-OMe are dissolved in a mixture of 6 ml of dioxane and 3 ml of water, and a total of 0.95 ml of 2N NaOH is added in portions, at 0° C. and within the space of 2 h. After the reaction is complete, the mixture is buffered by adding a little solid carbon dioxide and the Fmoc elimination, which has taken place to a small extent, is reversed by adding 50 mg of Fmoc-ONSU and subsequently stirring for 45 minutes. The mixture is then adjusted to pH 6.5 with 0.5 ml of a 2M solution of sodium hydrogen sulfate. Most of the dioxane is subsequently distilled off in vacuo, and the solution is diluted with water and overlaid with ethyl acetate. The mixture is acidified to pH 5, while being cooled with ice water, by adding a solution of potassium hydrogen sulfate. The organic phase is separated off and the aqueous phase is extracted a further two times with ethyl acetate. The combined organic phases are dried over sodium sulfate and concentrated in vacuo on a rotary evaporator, whereupon the product precipitates out. The product is filtered off and dried in vacuo.

Yield: 485 mg $R_F$: 0.55 (n-butanol/pyridine/acetic acid/water 8:2:2:10)

MS(FAB DMSO/NBA): 592 $(M^+)$

EXAMPLE 31

Fmoc-Aeg(T)-OMe 11.73 g of Fmoc-Aeg-OMe.HCl are dissolved, together with 5.52 g of thyminylacetic acid, in 100 ml of dry DMF, and 9.84 g of TOTU and 20.4 ml of diisopropylethylamine are then added one after the other. The mixture is stirred at room temperature for 3 h and then concentrated in vacuo on a rotary evaporator. The residue is taken up in ethyl acetate and this mixture is extracted three times, in each case, with a solution of sodium hydrogen carbonate and with a solution of potassium hydrogen sulfate. The organic phase is concentrated and the residue is dissolved in a little ethyl acetate; ether is added to the solution, whereupon the product precipitates out.

Yield: 12.3 g $R_F$: 0.62 (n-butanol/acetic acid/water 3:1:1)

MS($ES^+$): 521.4$(M+H)^+$

EXAMPLE 32

Fmoc-Aeg(T)-OH 12.0 g of Fmoc-Aeg(T)-OMe are suspended in a mixture of 100 ml of dioxane and 50 ml of water, and hydrolyzed by the portion-wise addition of 32 ml of 2N NaOH. After the reaction is complete, the mixture is buffered by adding a little solid carbon dioxide, and the partial Fmoc elimination which has taken place is reversed by adding 2.7 g of Fmoc-ONSU. The mixture is then filtered and the filtrate is extracted with ethyl acetate. The aqueous phase is adjusted to pH 2 with 1N NCl, whereupon the product precipitates out. The precipitate is filtered off with suction and dried in vacuo (crude product 11.6 g ). In order to remove salts, the crude product is taken up, while warming gently, in 70 ml of DMF, and undissolved material is filtered off and the filtrate is concentrated to dryness. The residue is taken up in ethyl acetate and precipitated by adding diisopropyl ether. The product is filtered off with suction and dried in vacuo.

Yield: 10.4 g $R_F$: 0.40 (n-butanol/acetic acid/water 3:1:1)

MS($ES^+$): 507.3 $(M+H)^+$

EXAMPLE 33

3-Benzyloxymethyl-2,4-dihydroxy-5-methylpyrimidineacetic acid

3-Benzyloxymethylthyminylacetic acid 13.65 g of ethyl 3-benzyloxymethyl-2,4-dihydroxy-5-methylpyrimidineacetate are dissolved in a mixture of 400 ml of dioxane, 200 ml of water, 100 ml of methanol and 40 ml of 1N NaOH. After the mixture has been stirred at room temperature for 2 h, the hydrolysis is complete. The mixture is concentrated down, in vacuo on a rotary evaporator, to a volume of approximately 200 ml, after which 200 ml of water are added and the mixture is extracted once with 100 ml of ethyl acetate (is discarded). The aqueous phase is adjusted to pH 1.5 with 1N HCl and extracted three times with 100 ml of ethyl acetate. The ethyl acetate phases are combined and dried over sodium sulfate. After filtering off the drying agent, the filtrate is concentrated to dryness. A viscous oil remains which is employed directly for the next reaction. After having been left to stand for a relatively long period, the oil becomes solid.

Yield: 11.35 g $R_F$: 0.64 (2-butanone/pyridine/water/acetic acid 70:15:15:2)

MS(ES$^+$): 305.2 (M+H)$^+$

EXAMPLE 34

Methyl N-(3-benzyloxymethyl-2,4-dihydroxy-5-methylpyrimidin-1-ylacetyl)-N-2-(9-fluorenylmethyloxycarbonylamino)ethylglycine Fmoc-Aeg (T$^{Bom}$)-OMe 3.04 g of 3-benzyloxymethyl-2,4-dihydroxy-5-methylpyrimidineacetic acid are dissolved in 100 ml of dry DMF, and 3.9 g of Fmoc-Aeg-OMe.HCl, 3.28 g of TOTU and 5.1 ml of diisopropylethylamine are added one after the other. The mixture is stirred at room temperature for 2 h and then concentrated to dryness in vacua on a rotary evaporator. The residue is taken up in ethyl acetate and this mixture is extracted three times, in each case, with a solution of sodium hydrogen carbonate and with a solution of potassium hydrogen sulfate. The organic phase is dried over sodium sulfate and concentrated after having filtered off the drying agent. The remaining, frothy residue is triturated with petroleum ether, filtered off with suction and dried in vacuo.

Yield: 4.68 g $R_F$: 0.75 (n-butanol/acetic acid/water 3:1:1)

MS(ES$^+$): 641.4(M+H)$^+$

EXAMPLE 35

N-(3-Benzyloxymethyl-2,4-dihydroxy-5-methylpyrimidin-1-ylacetyl)-N-2-(9-fluorenylmethyloxycarbonylamino) ethylglycine Fmoc-Aeg (T$^{Bom}$)-OH 2.3 g of Fmoc-Aeg(T$^{Bom}$)-oMe are dissolved in a mixture of 30 ml of dioxane and 15 ml of water, and hydrolyzed by the portion-wise addition of 7.36 ml of 1N NaOR. After the reaction is complete, the mixture is buffered by adding a little solid carbon dioxide, and the partial Fmoc elimination which has taken place is reversed by adding 0.41 g of Fmoc-ONSU. The mixture is then filtered and the dioxane is distilled off in vacuo on a rotary evaporator; the residual solution is diluted with 30 ml of water and the resulting solution, which is still alkaline, is extracted once with ethyl acetate. The aqueous phase is adjusted to pH 3 with 1N HCl, whereupon the product precipitates out. After the mixture has been left to stand at 4° C. in a cold room overnight, the precipitate is filtered off with suction and dried in vacuo. Additional product precipitates out from the filtrate after the latter has been concentrated to a smaller volume.

Yield: 1.47 g $R_F$: 0.37 (n-butanol/acatic acid/water 3:1:1)

MS(ES$^+$): 627.2(M+H)$^+$

PNA Syntheses

EXAMPLE 36

| H-(Aeg(T))$_8$-Lys-NH$_2$ | (C$_{49}$H$_{127}$N$_{35}$O$_{33}$, formula weight 2275.26) |
|---|---|

The synthesis is effected on an aminomethyl-polystyrene resin, using 5-(Fmoc-amino-4-methoxybenzyl)-2,4-dimethoxyphenypropionic acid as the anchor group, in a multiple peptide synthesizer from Abimed.

14.7 mg (10 μmol) of Fmoc-amide-anchor-resin are pre-swollen in DMF and introduced into a reaction vessel belonging to the multiple peptide synthesizer. The following reaction solutions are used in the synthesis:

1) Activator soln.: 0.876 molar solution of PyBOP in dried DMF
2) Base for activation: 3.95 molar solution of NEM in dried DMF
3) Fmoc-Lys(Boc)-OH: 0.65 molar in dried DMF
4) Fmoc-Aeg(T)-OH: 250 mg in 1 ml of dried DMF
5) Piperidine: 20% solution in DMF.

Following Fmoc elimination with the piperidine solution and washing with DMF, activator solution, Fmoc derivative and base are added to the deprotected resin in the reaction vessel. The coupling time is 40 min. After the reaction has been in progress for 28 min, 100 μl of dichloromethane are added. The resin is subsequently washed 5 times with DMF and is ready for the next treatment with piperidine. After the final elimination of Fmoc, the resin is dried and treated in portions with a total of 4 ml of 95% TFA (approximately 2.5 h). The TFA solution is concentrated in vacuo, and the residue is dissolved in 250 μl of TFA. This solution is apportioned between 5 Eppendorf tubes and precipitated using 600 μl of methyl tert-butyl ether per tube. The precipitate is sedimented by centrifugation and the supernatant is then decanted off. The precipitate is suspended in a little methyl tert-butyl ether and sedimented once again by centrifugation; the supernatant is then decanted off once more. This procedure is repeated once again and the product is then dried in vacuo. Purification is effected by means of chromatography on a ®MonoQ column (from Pharmacia, Munzingen) using a 0.17–0.44 M sodium chloride gradient in 10 mM NaOH (pH 12) and desalting by means of ultrafiltration.

Yield: 198 OD$_{260}$.

MS(FAB, AcOH/NBA): 2298(M+Na)$^+$

EXAMPLE 37

| H-(Aeg(T$^{triazolo}$))$_8$-Lys-NH$_2$ | (C$_{110}$H$_{134}$N$_{58}$O$_{26}$, formula weight 2682.65) |
|---|---|

The synthesis is effected on an aminomethyl-polystyrene resin, using 5-(Fmoc-amino-4-methoxyberzyl)-2,4-dimethoxyphenylpropionic acid as the anchor group, in a 380B ABI DNA synthesizer. 14.7 mg (10 μmol) of Fmoc-amide-anchor-resin are reacted, with program control, in a small synthesis column by means of adding the following solutions:

Position 1: Fmoc-lys(Boc)-OH: 0.66 molar solution in DMF
Position 2: Fmoc-Aeg(T$^{rriazolo}$)-OH: 735 mg in 2 ml of dried DMF
Position 5: Mixture of 1.35 ml of NEM and 1.7 ml of DMF (3.46 molar)
Position 6: PyBOP: 0.91 molar solution in dried DMF
Position 14: 20% piperidine in DMF
Position 16: DMF for washing the resin.
Position 17: DMF (dried) for reaction The quantity used for charging is adjusted by way of the flow rate to a 5-fold excess of lysine derivative or aminoethyl glycine derivative. The coupling is in each case carried out twice. In order to cleave the compound off the resin, a total of approximately 5 ml of 90% TFA is pushed manually through the small column within the space of 2 h. The TFA is concentrated in vacuo and the residue is dissolved in 300 μl of TFA; this solution is apportioned between 6 Eppendorf tubes. The product is precipitated by adding 1 ml of methyl tert-butyl ether to each tube. The precipitate is sedimented by centrifugation and the supernatant is then decanted off. The precipitate is suspended in a little methyl tert-butyl ether and sedimented once again by centrifugation, and the supernatant is decanted off once more. This procedure is repeated once again and the product is then dried in vacuo. Finally, it is suspended once again in methyl tert-butyl ether, centrifuged down and dried.

Yield: 270 $OD_{260}$.
MS(FAB, TFA/NBA): 2684 ($M^+$)

EXAMPLE 38

H-(Aeg(C))$_7$-Lys-NH$_2$ ($C_{76}H_{106}N_{38}O_{22}$, formula weight 1903.92)

The synthesis is carried out as described in EXAMPLE 36 but using 750 mg of Fmoc-Aeg($C^{Mmt}$)-OH, which is dissolved in 1.5 ml of dried DMF. cleaving-off and precipitation are carried out as described above.

Yield: 16 mg or 218 $OD_{260}$
MS(FAB, TFA/NBA): 1905 $(M+H)^+$

EXAMPLE 39

Ac-Aeg(A)-Aeg(C)-Aeg(A)-Aeg(T)-Aeg(C)-Aeg
(A)-Aeg(T)-Aeg(G)-Aeg(G)-Aeg(T)-Aeg(C)-Aeg
(G)-Lys-NH$_2$ ($C_{137}H_{176}N_{72}O_{38}$, formula weight 3439.39)

The PNAs are synthesize on an Ecosyn D-300 DNA synthesizer (from Eppendorf/Biotronik, Maintal) using 100 mg (5 μmol) of an aminopropyl-CPG which is loaded with 5-(Fmoc-amino-4-methoxybenzyl)-2,4-dimethoxyphenylpropionic acid as anchor group.

The following solutions were employed for the synthesis:
1) Activator soln.: 0.3 molar HATU solution in dried DMF
2) Base for activation: 0.3 molar solution of NEM in dried DMF
3) Fmoc-Lys(Boc)-OH: 0.3 molar solution in DMF
4) Elimination of Fmoc: 20% solution of piperidine in DMF
5) Fmoc-Aeg(T)-OH: 0.3 molar solution in dried DMF
6) Fmoc-Aeg($A^{Mmt}$)-OH: 0.3 molar solution in dried DMF
7) Fmoc-Aeg($C^{Mmt}$)-OH: 0.3 molar solution in dried DMF
8) Fmoc-Aeg($G^{Mmt}$)-OH: 0.3 molar solution in dried DMF After Fmoc elimination with piperidine solution and washing with DMF, activator solution, Fmoc derivative and base are added to the deprotected support in the reaction vessel. The coupling time is 20 min. The CPG is subsequently washed 5 times with DMF and is ready for the next treatment with piperidine. After the synthesis has finished, the PNA-CPG support is dried and worked up as described above.

Yield: 210 $OD_{260}$.
MS 3439.4 ($ES^+$): $(M)^+$

EXAMPLE 40

H-Asp-Aeg(C)-Aeg(C)-Aeg(A)-Aeg(T)-Aeg(G)-
Aeg(G)-Aeg(T)-Aeg(C)-Aeg(C)-Aeg(C)Asp-NH-
$(CH_2)_6$-OH ($C_{119}H_{157}N_{57}O_{38}$, formula weight 2993.94)

The PNAs are synthesized on an Ecosyn D-300 DNA synthesizer (from Eppendorf/Biotronik, Maintal) using 133 mg (5 μmol) of an aminopropyl-CPG which is loaded with 6-methylaminohex-1-yl hemisuccinate.

The following solutions were employed for the synthesis:
1) Activator soln.: 0.3 molar HATU solution in dried DMF
2) Base for activation: 0.3 molar solution of NEM in dried DMF
3) Fmoc-Asp(OtBu)-OH: 0.3 molar solution in DMF
4) Elimination of Fmoc 20% solution of piperidine in DMF
5) Fmoc-Aeg(T)-OH: 0.3 molar solution in dried
6) Fmoc-Aeg($A^{Mmt}$)-OH: 0.3 molar solution in dried DMF
7) Fmoc-Aeg($C^{Mmt}$)-OH: 0.3 molar solution in dried DMF
8) Fmoc-Aeg($G^{Mmt}$)-OH: 0.3 molar solution in dried DMF After Fmoc elimination with piperidine solution and washing with DMF, activator solution, Fmoc derivative and base are added to the deprotected support in the reaction vessel. The coupling time is 20 min. The CPG is subsequently washed S times with DMP and is ready for the next treatment with piperidine. After the synthesis has finished, the PNA-CPG support is dried, and the Mmt protecting groups on the bases are first eliminated using 3% trichloroacetic acid, followed by the tert-butyl groups on the aspartic acids, which are eliminated using 60% TFA in dichloromethane. The PNA is then cleaved from the support by treating with conc. ammonia solution at 65° C., and is then worked up as described above.

Yield: 100 $OD_{260}$.
MS 2994.4 ($ES^+$): $(M+H)^+$

What is claimed is:

1. A compound of the formula IV

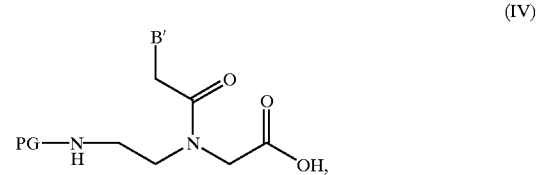

(IV)

in which
PG is a base-labile amino protecting group, and
B' is a nucleotide base, wherein when said nucleotide base has an exocyclic amino function, said function is protected by a protecting group which is compatible with the base-labile amino protecting group.

2. A compound of the formula IV as claimed in claim 1, wherein PG is the 9-fluorenylmethyloxycarbonyl (Fmoc), 2,2-[bis(4-nitrophenyl)]ethoxycarbonyl (Bnpeoc), or 2-(2,4-dinitrophenyl)ethoxycarbonyl (Dnpeoc) protecting group, and B' is a nucleotide base whose exocyclic amino function is protected by a protecting group which is labile to weak or medium-strength acids.

3. The compound of claim 2, wherein the protecting group for B' is tert-butyloxycarbonyl (Boc), 4-methoxybenzyloxycarbonyl (Moz), 3,5-dimethoxyphenyl-2-propyl-2-oxycarbonyl (Ddz), triphenylmethyl (Trt), (4-methoxyphenyl)diphenylmethyl (Mmt), (4-methylphenyl)-diphenylmethyl (Mtt), di-(4-methoxyphenyl)phenylmethyl (Dmt), or 9-(9-phenyl)xanthenyl) (pixyl).

4. The compound of claim 3 wherein the protecting group for B' is Boc, Trt, Mmt, Mtt, or Dmt.

5. The compound of claim 4, wherein the protecting group for B' is Trt, Mtt, Mmt, or Dmt.

6. The compound of claim 5, wherein the protecting group for B' is Mmt.

7. A compound of the formula IV as claimed in claim 1, wherein

PG is the Fmoc protecting group and

B' is a nucleotide base whose exocyclic amino function is protected by a protecting group which is labile to weak or medium-strength acids.

8. The compound of claim 7, wherein the protecting group for B' is tert-butyloxycarbonyl (Boc), 4-methoxybenzyloxycarbonyl (Moz), 3,5-dimethoxyphenyl-2-propyl-2-oxycarbonyl (Ddz), triphenylmethyl (Trt), (4-methoxyphenyl)diphenylmethyl (Mmt), (4-methylphenyl)-diphenylmethyl (Mtt), di-(4-methoxyphenyl)phenylmethyl (Dmt), or 9-(9-phenyl)xanthenyl) (pixyl).

9. The compound of claim 8, wherein the protecting group for B' is Boc, Trt, Mmt, Mtt, or Dmt.

10. The compound of claim 9, wherein the protecting group for B' is Trt, Mtt, Mmt, or Dmt.

11. The compound of claim 10, wherein the protecting group for B' is Mmt.

12. A process for preparing a compound of the formula IV,

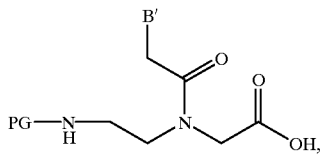
(IV)

in which PG is a base-labile amino protecting group and B' is a nucleotide base whose exocyclic amino function is protected by a protecting group which is compatible with the base-labile amino protecting group;

wherein said process comprises a) reacting, in a suitable solvent and at a temperature of 0–45° C., a compound of the formula V

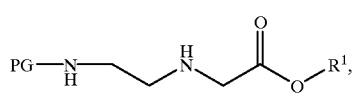
(V)

in which PG is a base-labile amino protecting group and $R^1$ is a group that protects the carboxylic acid function of formula V from chemical attack, with a compound of the formula VI

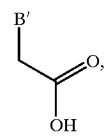
(VI)

in which B' is a nucleotide base whose exocyclic amino function is protected by a protecting group that is compatible with the base-labile amino protecting group wherein said reacting of a compound of formula V with a compound of formula VI is in the presence of a coupling agent that is customary in peptide synthesis, to yield a compound of the formula VII

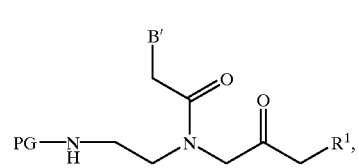
(VII)

in which PG, B', and $R^1$ are as described above;

b) hydrolyzing the ester group present in the compound of formula VII by treating the compound of formula VII with an alkali metal hydroxide solution, or by treating the compound of formula VII with at least one esterase or a lipase at in a suitable solvent at a temperature of 0–50° C. for a time and under conditions effective to produce a compound of formula IV; and c) isolating the compound of formula IV.

13. The process of claim 12, wherein the protecting group for B' is tert-butyloxycarbonyl (Boc), 4-methoxybenzyloxycarbonyl (Moz), 3,5-dimethoxyphenyl-2-propyl-2-oxycarbonyl (Ddz), triphenylmethyl (Trt), (4-methoxyphenyl)diphenylmethyl (Mmt), (4-methylphenyl)-diphenylmethyl (Mtt), di-(4-methoxyphenyl)phenylmethyl (Dmt), or 9-(9-phenyl)xanthenyl) (pixyl).

14. The process of claim 13, wherein the protecting group for B' is Boc, Trt, Mmt, Mtt, or Dmt.

15. The process of claim 14, wherein the protecting group for B' is Trt, Mtt, Mmt, or Dmt.

16. The process of claim 15, wherein the protecting group for B' is Mmt.

17. The process of claim 12, wherein the solvent for reacting the compound of formula V with the compound of formula VII is a mixture of more than one organic compound.

18. The process of claim 12, wherein the solvent for reacting the compound of formula V with the compound of formula VII is dimethylformamide (DMF), acetonitrile, dichloromethane, or a mixture of two or all of these solvents.

19. The process of claim 12, wherein the coupling agent is a carbodiimide, a phosphonium reagent, a uronium agent, an acid halide, or an active ester.

20. The process of claim 12, wherein the solvent for hydrolyzing the ester group present in the compound of formula VII is dioxane, water, tetrahydrofuran, methanol, or a mixture of two or more of these solvents.

21. The process of claim 12, wherein R' is methyl, ethyl, butyl, 2-(methoxyethoxy)ethyl, or benzyl.

22. The process of claim 12, wherein the protecting group for B' is labile to weak or medium-strength acids.

23. The process of claim 12, wherein the reaction of the compound of formula V with the compound of formula VI is performed at room temperature.

24. A process for preparing a compound of the formula IV,

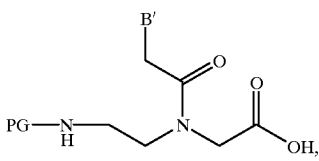
(IV)

in which PG is a base-labile amino protecting group and B' is a nucleotide base whose exocyclic amino function is protected by a protecting group which is compatible with the base-labile amino protecting group;

wherein said process comprises
a) reacting, in a suitable solvent and at a temperature of 0–40° C., a compound of the formula V

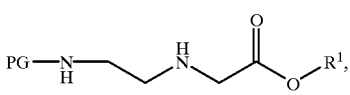
(V)

in which PG is a base-labile amino protecting group and R¹ is hydrogen or a temporary silyl protecting group, with a compound of the formula VIII

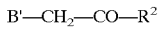
(VIII)

B'—CH₂—CO—R² in which B' is a nucleotide base whose exocyclic amino function is protected by a protecting group that is compatible with the base-labile amino protecting group, and R² is a halogen or the radical of an active ester; and
b) hydrolyzing the ester group present in the compound of formula VII by treating the compound of formula VII with an alkali metal hydroxide solution, or by treating the compound of formula VII with at least one esterase or a lipase at in a suitable solvent at a temperature of 0–50° C. for a time and under conditions effective to produce a compound of formula IV; and
c) isolating the compound of formula IV.

25. The process of claim 24, wherein the protecting group for B' is tert-butyloxycarbonyl (Boc), 4-methoxybenzyloxycarbonyl (Moz), 3,5-dimethoxyphenyl-2-propyl-2-oxycarbonyl (Ddz), triphenylmethyl (Trt), (4-methoxyphenyl)diphenylmethyl (Mmt), (4-methylphenyl)-diphenylmethyl (Mtt), di-(4-methoxyphenyl)phenylmethyl (Dmt), or 9-(9-phenyl)xanthenyl) (pixyl).

26. The process of claim 25, wherein the protecting group for B' is Boc, Trt, Mmt, Mtt, or Dmt.

27. The process of claim 26, wherein the protecting group for B' is Trt, Mtt, Mmt, or Dmt.

28. The process of claim 27, wherein the protecting group for B' is Mmt.

29. The process of claim 24, wherein the solvent for reacting the compound of formula V with the compound of formula VIII is a mixture of more than one organic compound.

30. The process of claim 24, wherein $R^1$ is hydrogen or trimethyl silyl.

31. The process of claim 24, wherein $R^2$ is fluorine, chlorine, bromine, or the radical of an active ester, wherein the active ester is a radical of 1-hydroxybenzotriazole (Obt), a radical of 3-hydroxy-4-oxo-3,4-dihydrobenzotriazin (OObt), a radical of pentafluorophenol (OPfp), or a radical of N-hydroxysuccinimide (ONSu).

32. The process of claim 24, wherein the reaction between the compound of formula V and the compound of formula VIII is performed at 20–30° C.

33. The process of claim 24, wherein the solvent for the reaction between the compound of formula V and the compound of formula VIII is dimethylfornamide (DMF), N-methylpyrrolidine (NMP), acetonitrile, dichloromethane, or mixtures of two or more of these solvents.

* * * * *

UNITED STATES PATENT AND TRADEMARK OFFICE
CERTIFICATE OF CORRECTION

PATENT NO. : 6,316,595 B1
DATED : November 13, 2001
INVENTOR(S) : Gerhard Breipohl et al.

It is certified that error appears in the above-identified patent and that said Letters Patent is hereby corrected as shown below:

Column 29,
Line 7, "claim 3 wherein" should read -- claim 3, wherein --.

Column 30,
Line 66, "R'" should read -- $R^1$ --.

Column 32,
Line 40, "dimethylfornamide" should read -- dimethylformamide --.

Signed and Sealed this

Twenty-first Day of May, 2002

Attest:

JAMES E. ROGAN
Attesting Officer
Director of the United States Patent and Trademark Office